United States Patent
Kawabe et al.

(10) Patent No.: US 7,125,842 B2
(45) Date of Patent: *Oct. 24, 2006

(54) ANTI-FUNGAL COMPOUNDS AND METHODS OF USE

(75) Inventors: Takumi Kawabe, Numazu (JP); Hidetaka Kobayashi, Numazu (JP)

(73) Assignee: CanBas Co. Ltd., Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/819,375

(22) Filed: Apr. 5, 2004

(65) Prior Publication Data

US 2004/0229801 A1  Nov. 18, 2004

Related U.S. Application Data

(60) Provisional application No. 60/461,109, filed on Apr. 7, 2003.

(51) Int. Cl.
*A01N 38/18* (2006.01)
*A61K 38/00* (2006.01)

(52) U.S. Cl. ............................................. 514/2; 930/20
(58) Field of Classification Search .................. 514/7
See application file for complete search history.

(56) References Cited

U.S. PATENT DOCUMENTS 5,696,078 A * 12/1997 Oppenheim et al. ........... 514/2
2004/0248783 A1* 12/2004 Kawabe et al. .............. 514/12

OTHER PUBLICATIONS

J. Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004).*
H.J.C. Berendsen. A Glimpse of the Holy Grail? Science (1998) 282, pp. 642-643.*
D. Voet and J.G. Voet. Biochemistry, 2nd Edition.(1995), pp. 235-241.*

* cited by examiner

*Primary Examiner*—Bruce R. Campell
*Assistant Examiner*—Thoams S. Heard
(74) *Attorney, Agent, or Firm*—Pillsbury Winthrop Shaw Pittman LLP

(57) ABSTRACT

The invention relates to compounds including peptides and peptidomimetics having anti-fungal activity alone, and in combination with other agents that have anti-fungal activity. The invention includes the use of cell cycle G2 checkpoint abrogators as anti-fungal agents, such as anti-fungal medicine.

61 Claims, 2 Drawing Sheets

SEQUENCE LISTING

<160> NUMBER OF SEQ ID NOS: 120

<210> SEQ ID NO 1
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Tyr Gly Gly Pro Gly Gly Gly Gly Asn
 1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Tyr Ser Leu Pro Pro Glu Leu Ser Asn Met
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Ala Arg Ser Ala Ser Met Pro Glu Ala Leu
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Tyr Arg Ser Pro Ser Met Pro Glu Asn Leu
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Tyr Arg Ser Pro Ala Met Pro Glu Asn Leu
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Trp Tyr Arg Ser Pro Ser Phe Tyr Glu Asn Leu
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Tyr Arg Ser Pro Ser Tyr Tyr Glu Asn Leu
 1               5                  10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Tyr Arg Ser Pro Ser Tyr Tyr
 1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Tyr Arg Ser Pro Ser Tyr Pro Glu Asn Leu
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Tyr Arg Ser Pro Ser Tyr Phe Glu Asn Leu
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Tyr Arg Ser Pro Ser Tyr Tyr Glu Asn Leu
 1               5                  10
```

```
<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Tyr Arg Ser Pro Ser Tyr Trp Glu Asn Leu
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Tyr Arg Ser Pro Ser Asn Pro Glu Asn Leu
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Tyr Arg Ser Pro Ser Asn Phe Glu Asn Leu
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Tyr Arg Ser Pro Ser Asn Tyr Glu Asn Leu
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Tyr Arg Ser Pro Ser Asn Trp Glu Asn Leu
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Leu Tyr Arg Ser Pro Ser His Pro Glu Asn Leu
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Tyr Arg Ser Pro Ser His Phe Glu Asn Leu
 1               5                  10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Tyr Arg Ser Pro Ser His Tyr Glu Asn Leu
 1               5                  10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Tyr Arg Ser Pro Ser His Trp Glu Asn Leu
 1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Tyr Ser Ser Pro Ser Met Pro Glu Asn Leu
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Tyr Ser Ser Pro Ser Met Phe Glu Asn Leu
 1               5                  10
```

```
<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Tyr Ser Ser Pro Ser Met Tyr Glu Asn Leu
 1               5                  10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Tyr Ser Ser Pro Ser Met Trp Glu Asn Leu
 1               5                  10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Tyr Ser Ser Pro Ser Phe Pro Glu Asn Leu
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Tyr Ser Ser Pro Ser Phe Pro Glu Asn Leu
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Tyr Ser Ser Pro Ser Phe Phe Glu Asn Leu
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 28

Leu Tyr Ser Ser Pro Ser Phe Tyr Glu Asn Leu
 1               5                  10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Tyr Ser Ser Pro Ser Phe Trp Glu Asn Leu
 1               5                  10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Tyr Ser Ser Pro Ser Tyr Pro Glu Asn Leu
 1               5                  10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Tyr Ser Ser Pro Ser Tyr Phe Glu Asn Leu
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Tyr Ser Ser Pro Ser Tyr Tyr Glu Asn Leu
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Tyr Ser Ser Pro Ser Tyr Trp Glu Asn Leu
 1               5                  10
```

```
<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Tyr Ser Ser Pro Ser Gln Pro Glu Asn Leu
 1               5                  10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Tyr Ser Ser Pro Ser Gln Trp Glu Asn Leu
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Tyr Ser Ser Pro Ser His Pro Glu Asn Leu
 1               5                  10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Tyr Ser Ser Pro Ser His Phe Glu Asn Leu
 1               5                  10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Tyr Ser Ser Pro Ser His Tyr Glu Asn Leu
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Leu Tyr Ser Ser Pro Ser His Trp Glu Asn Leu
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Tyr Thr Ser Pro Ser Met Pro Glu Asn Leu
 1               5                  10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Tyr Thr Ser Pro Ser Met Phe Glu Asn Leu
 1               5                  10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Tyr Thr Ser Pro Ser Met Tyr Glu Asn Leu
 1               5                  10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Tyr Thr Ser Pro Ser Met Trp Glu Asn Leu
 1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Tyr Thr Ser Pro Ser Phe Pro Glu Asn Leu
 1               5                  10
```

```
<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Tyr Thr Ser Pro Ser Phe Phe Glu Asn Leu
  1               5                  10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Tyr Thr Ser Pro Ser Phe Tyr Glu Asn Leu
  1               5                  10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Tyr Thr Ser Pro Ser Phe Trp Glu Asn Leu
  1               5                  10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Tyr Thr Ser Pro Ser Tyr Pro Glu Asn Leu
  1               5                  10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Tyr Thr Ser Pro Ser Tyr Phe Glu Asn Leu
  1               5                  10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 50

Leu Tyr Thr Ser Pro Ser Tyr Tyr Glu Asn Leu
  1               5                  10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Tyr Thr Ser Pro Ser Tyr Trp Glu Asn Leu
  1               5                  10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Tyr Thr Ser Pro Ser Asn Pro Glu Asn Leu
  1               5                  10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Tyr Thr Ser Pro Ser Asn Phe Glu Asn Leu
  1               5                  10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Tyr Thr Ser Pro Ser Asn Tyr Glu Asn Leu
  1               5                  10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Tyr Thr Ser Pro Ser Asn Trp Glu Asn Leu
  1               5                  10
```

```
<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Tyr Thr Ser Pro Ser His Pro Glu Asn Leu
 1               5                  10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Tyr Thr Ser Pro Ser His Phe Glu Asn Leu
 1               5                  10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Tyr Thr Ser Pro Ser His Tyr Glu Asn Leu
 1               5                  10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Tyr Thr Ser Pro Ser His Trp Glu Asn Leu
 1               5                  10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Tyr His Ser Pro Ser Tyr Pro Glu Asn Leu
 1               5                  10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 61

Leu Tyr His Ser Pro Ser Tyr Phe Glu Asn Leu
 1               5                  10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Tyr His Ser Pro Ser Tyr Tyr Glu Asn Leu
 1               5                  10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Tyr His Ser Pro Ser Tyr Trp Glu Asn Leu
 1               5                  10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Phe Thr Ser Pro Ser Tyr Pro Glu Asn Leu
 1               5                  10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Phe Thr Ser Pro Ser Tyr Phe Glu Asn Leu
 1               5                  10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Phe Thr Ser Pro Ser Tyr Tyr Glu Asn Leu
 1               5                  10
```

```
<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Phe Thr Ser Pro Ser Tyr Trp Glu Asn Leu
 1               5                  10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Tyr Ser Ser Pro Ser His Pro Glu Asn Leu
 1               5                  10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Phe Tyr Ser Ser Pro Ser His Phe Glu Asn Leu
 1               5                  10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Phe Tyr Ser Ser Pro Ser His Tyr Glu Asn Leu
 1               5                  10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Phe Tyr Ser Ser Pro Ser His Trp Glu Asn Leu
 1               5                  10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 72

Phe Tyr Thr Ser Pro Ser Met Pro Glu Asn Leu
  1               5                  10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Phe Tyr Thr Ser Pro Ser Met Phe Glu Asn Leu
  1               5                  10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Tyr Thr Ser Pro Ser Met Tyr Glu Asn Leu
  1               5                  10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Tyr Thr Ser Pro Ser Met Trp Glu Asn Leu
  1               5                  10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Phe Tyr Thr Ser Pro Ser Phe Pro Glu Asn Leu
  1               5                  10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Phe Tyr Thr Ser Pro Ser Phe Phe Glu Asn Leu
  1               5                  10
```

```
<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Tyr Thr Ser Pro Ser Phe Tyr Glu Asn Leu
 1               5                  10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Tyr Thr Ser Pro Ser Phe Trp Glu Asn Leu
 1               5                  10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Phe Tyr Thr Ser Pro Ser Tyr Pro Glu Asn Leu
 1               5                  10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Tyr Thr Ser Pro Ser Tyr Phe Glu Asn Leu
 1               5                  10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Tyr Thr Ser Pro Ser Tyr Tyr Glu Asn Leu
 1               5                  10

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 83

Phe Tyr Thr Ser Pro Ser Tyr Trp Glu Asn Leu
 1               5                  10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Tyr Arg Ser Pro Ser Met Pro Glu Asn Leu
 1               5                  10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Tyr Arg Ser Pro Ser Met Phe Glu Asn Leu
 1               5                  10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Trp Tyr Arg Ser Pro Ser Met Tyr Glu Asn Leu
 1               5                  10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Trp Tyr Arg Ser Pro Ser Met Trp Glu Asn Leu
 1               5                  10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Trp Tyr Arg Ser Pro Ser Phe Pro Glu Asn Leu
 1               5                  10
```

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Tyr Arg Ser Pro Ser Phe Phe Glu Asn Leu
 1               5                  10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Trp Tyr Arg Ser Pro Ser Phe Tyr Glu Asn Leu
 1               5                  10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Tyr Arg Ser Pro Ser Phe Trp Glu Asn Leu
 1               5                  10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Tyr Arg Ser Pro Ser Tyr Pro Glu Asn Leu
 1               5                  10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Tyr Arg Ser Pro Ser Tyr Phe Glu Asn Leu
 1               5                  10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 94

Trp Tyr Arg Ser Pro Ser Tyr Tyr Glu Asn Leu
  1               5                  10

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Tyr Arg Ser Pro Ser Tyr Trp Glu Asn Leu
  1               5                  10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Trp Tyr Thr Ser Pro Ser Met Pro Glu Asn Leu
  1               5                  10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Trp Tyr Thr Ser Pro Ser Met Phe Glu Asn Leu
  1               5                  10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Tyr Thr Ser Pro Ser Met Tyr Glu Asn Leu
  1               5                  10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Trp Tyr Thr Ser Pro Ser Met Trp Glu Asn Leu
  1               5                  10
```

```
<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Tyr Thr Ser Pro Ser Phe Pro Glu Asn Leu
  1               5                  10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Trp Tyr Thr Ser Pro Ser Phe Phe Glu Asn Leu
  1               5                  10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Trp Tyr Thr Ser Pro Ser Phe Tyr Glu Asn Leu
  1               5                  10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Trp Tyr Thr Ser Pro Ser Phe Trp Glu Asn Leu
  1               5                  10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Trp Tyr Thr Ser Pro Ser Tyr Pro Glu Asn Leu
  1               5                  10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 105

Trp Tyr Thr Ser Pro Ser Tyr Phe Glu Asn Leu
 1               5                  10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Tyr Thr Ser Pro Ser Tyr Tyr Glu Asn Leu
 1               5                  10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Trp Tyr Thr Ser Pro Ser Tyr Trp Glu Asn Leu
 1               5                  10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Trp Tyr Thr Ser Pro Ser His Pro Glu Asn Leu
 1               5                  10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Trp Tyr Thr Ser Pro Ser His Phe Glu Asn Leu
 1               5                  10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Trp Tyr Thr Ser Pro Ser His Tyr Glu Asn Leu
 1               5                  10
```

```
<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Trp Tyr Thr Ser Pro Ser His Trp Glu Asn Leu
 1               5                  10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Lys Arg Ser Pro Ser Met Pro Glu Asn Leu
 1               5                  10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Leu Tyr Ile Ser Pro Ser Met Pro Glu Asn Leu
 1               5                  10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Tyr Arg Ser Pro Ser Met Val Glu Asn Leu
 1               5                  10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Gly Arg Lys Lys Arg Arg Gln Arg Arg Arg
 1               5                  10

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (12)
<223> OTHER INFORMATION: l-Cha
<220> FEATURE:
<221> NAME/KEY: MOD_RES
<222> LOCATION: (13)
<223> OTHER INFORMATION: l-Phe-2,3,4,5,6-F

<400> SEQUENCE: 116

Tyr Gly Arg Lys Lys Arg Arg Gln Arg Arg Xaa Xaa Arg Ser Pro
 1               5                  10                  15

Ser Tyr Tyr

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: l-Cha
<220> FEATURE:
<221> NAME/KEY: MOD_RES
<222> LOCATION: (13)
<223> OTHER INFORMATION: l-Phe-2,3,4,5,6-F

<400> SEQUENCE: 117

Tyr Gly Arg Lys Lys Arg Arg Gln Arg Arg Xaa Xaa Arg Ser Pro
 1               5                  10                  15

Ser Tyr

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: l-Cha
<220> FEATURE:
<221> NAME/KEY: MOD_RES
<222> LOCATION: (5)
<223> OTHER INFORMATION: l-Phe-2,3,4,5,6-F

<400> SEQUENCE: 118

Arg Arg Arg Xaa Xaa Arg Ser Pro Ser Tyr Tyr
 1               5                  10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: l-Cha
<220> FEATURE:
<221> NAME/KEY: MOD_RES
<222> LOCATION: (8)
<223> OTHER INFORMATION: l-Phe-2,3,4,5,6-F
```

```
-continued

<400> SEQUENCE: 119

Arg Arg Gln Arg Arg Arg Xaa Xaa Arg Ser Pro Ser Tyr Tyr
1               5                   10

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: l-Cha
<220> FEATURE:
<221> NAME/KEY: MOD_RES
<222> LOCATION: (13)
<223> OTHER INFORMATION: l-Phe-2,3,4,5,6-F
<220> FEATURE:
<221> NAME/KEY: MOD_RES
<222> LOCATION: (14)
<223> OTHER INFORMATION: l-aminoundecanoic acid

<400> SEQUENCE: 120

Tyr Gly Arg Lys Lys Arg Arg Gln Arg Arg Arg Xaa Xaa Xaa Tyr Tyr
1               5                   10                  15
```

US 7,125,842 B2

ANTI-FUNGAL COMPOUNDS AND METHODS OF USE

RELATED APPLICATIONS

This application claims priority to application Ser. No. 60/461,109, filed Apr. 7, 2003, which is incorprated herein by reference.

TECHNICAL FIELD

The invention relates to compounds including peptides and peptidomimetics having anti-fungal activity alone, and combinations with other agents that have anti-fungal activity. The invention includes the use of cell cycle G2 checkpoint abrogators as anti-fungal agents, such as anti-fungal medicine.

BACKGROUND

The cell cycle comprises S phase (DNA replication), M phase (mitosis), and two gap phases (G1 and G2 phases) between S and M phases. Checkpoints in the cell cycle ensure accurate progression, such as monitoring the state of DNA integrity, DNA replication, cell size, and the surrounding environment (Maller, J. L. Curr. Opin. Cell Biol., 3:26 (1991)). It is especially important for multi-cellular organisms to maintain integrity of genome, and there are multiple checkpoints that monitor the state of genome. Among them are G1 and G2 checkpoints existing before DNA replication and mitosis, respectively. It is crucial to correct DNA damage before entering S phase for multicellular organisms, because once damaged DNA is replicated it often gives rise to mutations (Hartwell, L. Cell, 71: 543 (1992)). Progression through G1 and G2 checkpoints without repairing extensive DNA damage induces apoptosis and/or catastrophe.

Most cancer cells carry abnormalities in G1 checkpoint-related proteins such as p53, Rb, MDM-2, p16$^{INK4}$ and p19$^{ARF}$ (Levine, A. J. Cell, 88:323 (1997)). Abrogated G1 checkpoint contributes to higher mutation rates and the many mutations observed in cancer cells. As a result, most cancer cells depend on G2 checkpoint for survival against excessive DNA damage (O'Connor and Fan, Prog. Cell Cycle Res., 2:165 (1996)). This state is similar to unicellar organisms such as yeasts and fungus which does not have strict cell cycle G1 checkpoint and have strict G2 checkpoint. The unicellular organisms can survive as a species if only one of them could adopt circumstantial change by obtaining advantageous mutations. The low stringency at G1 checkpoint especially against DNA damage is advantageous to get favorable mutations.

The mechanism that promotes the cell cycle G2 arrest after DNA damage is believed to be conserved among species from yeast to human. In the presence of damaged DNA, Cdc2/Cyclin B kinase is kept inactive because of inhibitory phosphorylation of threonine-14 and tyrosine-15 residues on Cdc2 kinase or the protein level of Cyclin B is reduced. At the onset of mitosis, the dual phosphatase Cdc25 removes these inhibitory phosphates and thereby activates Cdc2/Cyclin B kinase. The activation of Cdc2/Cyclin B is equivalent to the onset of M phase.

In fission yeast, the protein kinase Chk1 is required for the cell cycle arrest in response to damaged DNA. Chk1 kinase acts downstream of several rad gene products including rad3 (orthologue of human ATM) and is modified by the phosphorylation upon DNA damage. The kinases Rad53 of budding yeast and Cds1 of fission yeast are known to conduct signals from unreplicated DNA. It appears that there is some redundancy between Chk1 and Cds1 because elimination of both Chk1 and Cds1 culminated in disruption of the G2 arrest induced by damaged DNA. Both Chk1 and Cds1 phosphorylate Cdc25 and promote Rad24 (orthologue of human 14-3-3) binding to Cdc25, which sequesters Cdc25 to cytosol and prevents Cdc2/Cyclin B activation. Cdc25 appears to be a target of these kinases.

SUMMARY

This invention provides anti-fungal compounds, including peptides and peptidomimetics, and methods of using the anti-fungal compounds. The invention anti-fungal compounds are useful for treating fungus (e.g. to kill or inhibit growth of yeast, mold, slimes). These compounds can be used to treat any object or organism having or at risk of having undesirable fungal contact, contamination, growth, proliferation or infection. For example, the compounds can be used to treat subjects, including mammals such as humans, having or at risk of having fungal growth or a fungal infection.

Invention compounds may be combined with other treatments or agents, including anti-fungal treatments, and other treatment methods. Particular non-limiting examples of anti-fungal treatments include, for example, anti-fungal agents or nucleic acid damaging treatments. Combination compositions including an invention composition and an anti-fungal agent can be used to decrease, reduce or inhibit fungal contact, contamination, growth, proliferation or infection. Thus, the compounds of the invention can be used alone or in combination with other anti-fungal treatments in accordance with the methods set forth herein.

The invention therefore provides methods of inhibiting or reducing fungal infection or fungal growth. In one embodiment, a method includes contacting the fungus or an object in contact with the fungus with an amount of a peptide or peptidomimetic sequence sufficient to inhibit or reduce fungal infection or fungal growth.

The invention further provides methods of inhibiting or reducing contamination of an object or organism with a fungus. In one embodiment, a method includes contacting the object or organism with an amount of a compound including a peptide or peptidomimetic sequence sufficient to inhibit or reduce contamination of the object with the fungus.

The invention also provides methods of treating fungal growth or fungal infection. In one embodiment, a method includes administering to a subject having or at risk of having fungal growth or fungal infection an amount of a compound comprising a peptide or peptidomimetic sequence sufficient to treat fungal growth or fungal infection.

The invention additionally provides methods of treating fungal growth, contamination or infection of a plant, plant part or seed having or at risk of having fungal growth, contamination or infection. In one embodiment, a method includes contacting the plant, plant part or seed having or at risk of having fungal growth, contamination or infection with an amount of a peptide or peptidomimetic sequence sufficient to treat fungal growth, contamination or infection.

Invention peptides and peptidomimetic sequences include sequences having 90% or more identity to a sequence defined as: P1, P2, P3, P4, P5, P6 or P6, P5, P4, P3, P2, P1; wherein P1 is d- or l-Cha, d- or l-Nal(2), d- or l-(Phe-2,3, 4,5,6-F), d- or l-(Phe-3,4,5F), d- or l-(Phe-4CF3), an amino acid that occupies a similar side chain space (e.g., d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene group, benzofuran, benzothiophene, quinoline, indoline, chroman, quinoxaline, quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4; P6 is d- or l-Bpa, d- or l-Phe$_4$NO$_2$, any amino acid and d- or l-Tyr (e.g., d-Ser-d-Tyr) any amino acid and d- or l-Phe (e.g., d-Ser-d-Phe), any amino acid, or nothing.

Invention peptides and peptidomimetic sequences further include sequences having 90% or more identity to a sequence defined as: P1, P2, P3, P4, P5, P6 or P6, P5, P4, P3, P2, P1; wherein P1 is d- or l-Cha, d- or l-Nal(2), d- or l-(Phe-2,3,4,5,6-F), d- or l-(Phe-3,4,5F), d- or l-(Phe-4CF3), an amino acid that occupies a similar side chain space (e.g., d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene group, benzofuran, benzothiophene, quinoline, indoline, chroman, quinoxaline, quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4; P6 is d- or l-Bpa, d- or l-Phe$_4$NO$_2$, any amino acid and d- or l-Tyr (e.g., d-Ser-d-Try), any amino acid and d- or l-Phe (e.g., d-Ser-d-Phe), any amino acid, or nothing.

In various aspects, the amino acid having a simple carbon chain is d- or l-11-aminoundecanoic acid, d- or l-10-aminodecanoic acid, d- or l-9-aminononanoic acid, d- or l-8-aminocaprylic acid, d- or l-7-aminoheptanoic acid, d- or l-6-aminocaproic acid, or a similar structure with one or more unsaturated carbon bonds.

Aspects of the invention include combination compositions of peptides and peptidomimetics with an anti-fungal treatment or agent. In one aspect, an anti-fungal treatment or agent is a nucleic acid damaging agent or nucleic acid damaging treatment. In particular, a peptide or peptidomimetic can be combined a with nucleic acid damaging agent, a nucleic acid damaging treatment, an anti-fungal agent, or an anti-fungal treatment for adminstration or delivery to a subject, or other organism or object.

Additional aspects of the invention include combination compositions of peptides and peptidomimetics with anti-inflammatory and anti-microbial treatments or agents. In particular, a peptide or peptidomimetic can be combined a with an anti-inflammatory or anti-microbial treatment or agent for adminstration or delivery to a subject, or other organism or object.

Agents and treatments include drugs, such as a chemotherapeutic drug, or a drug having an anti-fungal activity or an anti-fungal function. Agents and treatments include systemic as well as regional or topical drugs.

Specific examples of drugs are those within a chemical class that includes: allylamines, azoles, polyense, pyrimidines, tetraenes, thiocarbamates, sulfonamides, glucan synthesis inhibitors and benzoic acid compounds. Particular examples of such drugs include: amrolfine, butenafine, naftifine, terbinafine, ketoconazole, fluconazole, elubiol, econazole, econaxole, itraconazole, isoconazole, imidazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopirox olamine, haloprogin, undecylenate, silver sulfadiazine, undecylenic acid, undecylenic alkanolamide, Carbol-Fuchsin, and prodrugs thereof. Additional examples of such drugs include: 5-fluorouracil (5-FU), rebeccamycin, adriamycin (ADR), bleomycin (Bleo), pepleomycin, a cisplatin derivative, camptotecin (CPT), and prodrugs thereof.

The fungus can be present in or on an object or organism, e.g., a human subject or a plant. The object can be non-living. The object can be an inorganic material or an organic material. The fungus or object can be present in the environment, in a residential, commerical, industrial or community setting, or in an agricultural or horticultural setting. The organism can be a single or a plurality of cells. The cell can be a cultured cell or a cell in vivo or ex vivo.

Fungus includes a yeast, mold or slime. Particular yeast genera include *Candida* and *Saccharomyces*. Particular yeast include dermatophytes, *Coccidioides immitis, Histoplasma capsulatum, Candida albicans* and *Aspergillus fumigatus*.

Fungal growth or fungal infection can be present on a subject. Areas of fungal growth, infection, contact or contamination include, for example, the skin, toe, nail, hair or a mucosal tissue. Examples of mucosal tissue subject to fungal growth, contamination or infection include, for example, gastrointestinal tract, mouth, lungs, bronchial passages, nasal passages and sinuses, genito-urinary tract, and vagina.

The invention compositions and methods can be administered locally, regionally or systemically. The invention compositions can be administered prior to, substantially contemparaneously with or following fungal contact, contamination, growth or infection. The invention compositions can be administered to skin, toe, nail, hair or a mucosal tissue.

Fungal growth or fungal infection can cause various diseases or symptoms. Particular examples include onychomycosis; Jock-itch or athlete's foot; paracoccidioidomycosis; blastomycosis; mucormycosis; cryptococcosis; coccidioidomycosis; histoplasmosis; candidiasis; and aspergillosis.

The compositions and treatment methods can result in reducing, decreasing or inhibiting fungal growth, contamination, viability or infection. The compositions and treatment methods can result in reduced susceptibility to or recurrence of fungal growth, contamination or infection. The compositions and treatment methods can result in inhibiting a worsening or progression of fungal growth, contamination or infection.

Invention compositions and methods can lead to improving a treated subject's condition. Improvements include, for example, reduced irritation, itching, inflammation, burning, hives, weeping, pruritus, excess discharge, discoloration, headache, and fatigue; reduced susceptibility to or recurrence of fungal growth or fungal infection; and inhibiting a worsening or progression of the subject's condition.

Where the treatment is on a plant, plant part or seed, the contacting can be local, regional or systemic. Treatment on a plant, plant part or seed includes contacting with the sequence prior to, substantially contemporaneously with or following fungal growth, contamination or infection. The plant, plant part or seed can be present in the environment, in an industrial setting, in a community setting, in a residential setting, in a commercial setting, or in an agricultural or horticultural setting.

Examples of fungal growth, contamination or infection include black spot, glomerella, ripe spot, sooty blotch, septoria leaf spot, cercospora leaf spot, rust, downy mildew, brown rot, brown patch, a smut, verrucosisl, dead arm disease, mycosphaerella leaf spot, black spot (roses), flower blight, septoria leaf blight, early and late blight, leaf mould, anthracnose, ring spot, dollar spot, northern leaf blight, alternaria and leaspora spot.

Specific examples of agents and treatments that can be combined or used in combination compositions and methods on plants, trees, bushes, etc. include Banner Maxx, Compass Cleary's, Funginex, Immunox, Dithane, Eagle, Fore, Systhane, Topsin, captan, thiram, carboxin, mefenoxan, PCNB, fludioxonil, thiabendazole, a copper-based fungicide, a sulfur compound, a citrus oil and *Bacillus subtilis*.

The invention moreover provides methods for identifying and screening for compounds (e.g., peptides or peptidomimetics) having anti-fungal activity. In one embodiment, a method includes contacting a compund that abrogates or inhibits G2 checkpoint with a fungus; incubating the fungus with the compound; and determining viability, growth or proliferation of the fungus. Reduced viability, growth or proliferation of the fungus in the presence of the compound identifies the compound as having anti-fungal activity. In another embodiment, a method includes contacting a compund that abrogates or inhibits G2 checkpoint with a fungus; incubating the fungus with the compound; and determining viability, growth or proliferation of the fungus.

DETAILED DESCRIPTION

Figure 1:
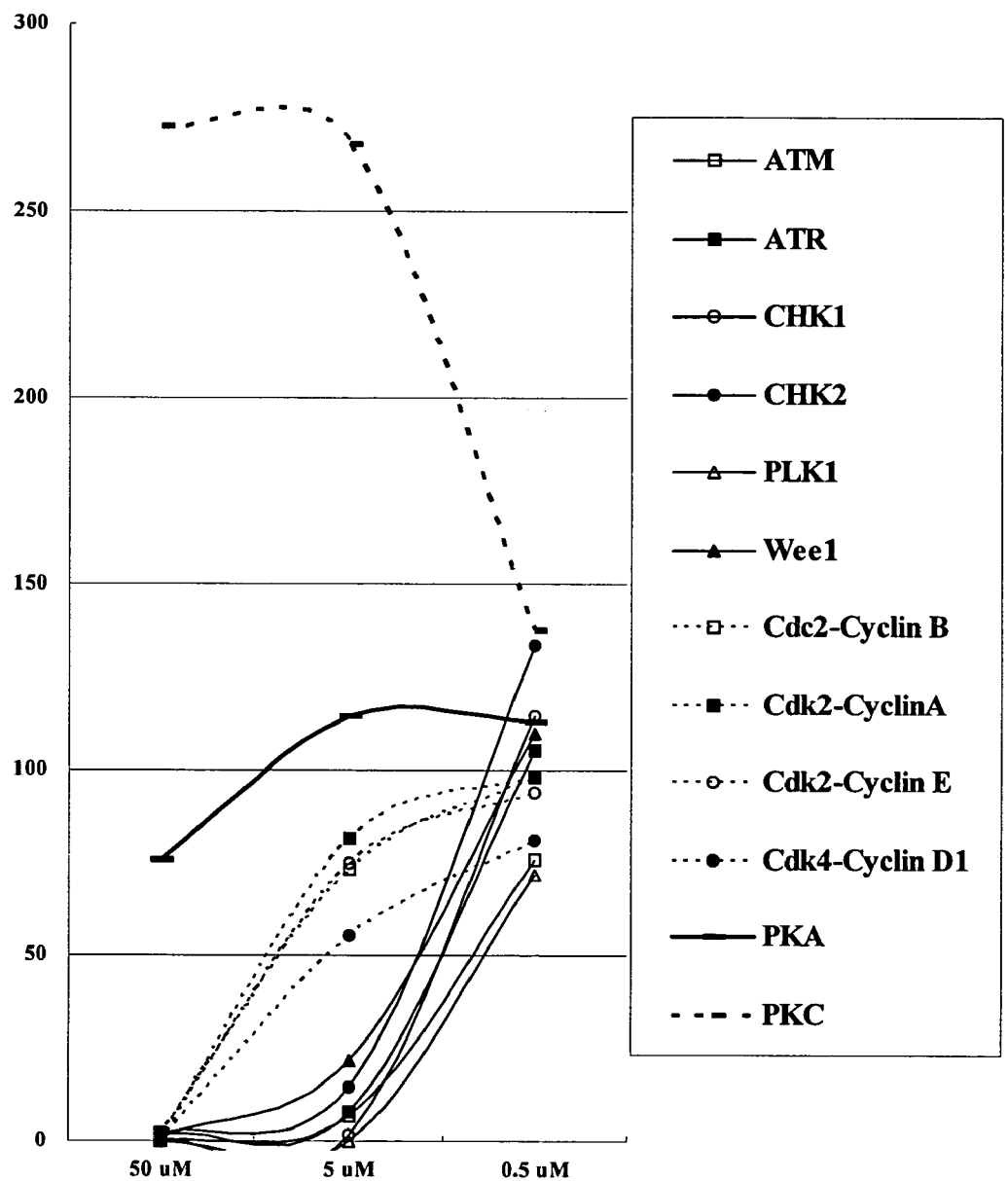
FIG. 1 shows the in vitro phosphorylation inhibition activity of CBP501 against various serine-threonine kinases. The Y-axis indicates the posphorylation of substrates by given kinases. 100% is the kinase activity without the compounds.

The invention provides compounds useful for treating fungal contact, contamination, growth, proliferation or infection, as well as disorders or conditions associated with or caused by fungal contact, contamination, growth, proliferation or infection. Compounds including peptides and peptidomimetics having anti-fungal activity or anti-fungal function are therefore provided, as well as methods of using the compounds to treat, reduce or inhibit fungal contact, contamination, growth, proliferation or infection, or reduce or decrease susceptibility to or recurrence of fungal contact, contamination, growth, proliferation or infection. Although not wishing to be bound by any theory, the ability of invention compounds including peptides and peptidomimetics to inhibit fungal contact, contamination, growth, proliferation or infection of yeast and other fungi appears to be due at least in part to abrogation of the cell cycle G2 checkpoint.

In one embodiment, an invention compound comprises a contiguous peptide or peptidomimetic sequence that includes the following structure: P1, P2, P3, P4, P5, P6 or P6, P5, P4, P3, P2, P1; wherein P1 is d- or l-Cha, d- or l-Nal(2), d- or l-(Phe-2,3,4,5,6-F), d- or l-(Phe-3,4,5F), d- or l-(Phe-4CF3), an amino acid that occupies a similar side chain space (e.g., d- or l-Tyr, d- or l-Phe), or any amino acid with one or two aromatic, piperidine, pyrazine, Pyrimidine, piperazine, morpholine or pyrimidine group(s), or one indole, pentalene, indene, naphthalene group, benzofuran, benzothiophene, quinoline, indoline, chroman, quinoxaline, quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4; P6 is d- or l-Bpa, d- or l-Phe$_4$NO$_2$, any amino acid and d- or l-Tyr (e.g., d-Ser-d-Tyr), any amino acid and d- or l-Phe (e.g., d-Ser-d-Phe), any amino acid, or nothing. In various aspects, the amino acid having a simple carbon chain is d- or l-11-aminoundecanoic acid, d- or l-10-aminodecanoic acid, d- or l-9-aminononanoic acid, d- or l-8-aminocaprylic acid, d- or l-7-aminoheptanoic acid, d- or l-6-aminocaproic acid, or a similar structure with one or more unsaturated carbon bonds.

In another embodiment, an invention compound comprises a contiguous peptide or peptidomimetic sequence that includes the following structure: P1, P2, P3, P4, P5, P6; P6, P5, P4, P3, P2, P1; P1, P2, P3, P4, P5, P6, P7, P8, P9, P10, P11, P12; P1, P2, P3, P4, P5, P6, P12, P11, P10, P9, P8, P7; P6, P5, P4, P3, P2, P1, P7, P8, P9, P10, P11, P12; P6, P5, P4, P3, P2, P1, P12, P11, P10, P9, P8, P7; P7, P8, P9, P10, P11, P12, P1, P2, P3, P4, P5, P6, P7, P8, P9, P10, P11, P12, P6, P5, P4, P3, P2, P1; P12, P11, P10, P9, P8, P7, P1, P2, P3, P4, P5, P6; P12, P11, P10, P9, P8, P7, P6, P5, P4, P3, P2, P1; P12, P11, P6, P9, P8, P7, P2, P1; P12, P11, P10, P6, P9, P4, P7, P2, P1; P1, P2, P7, P8, P9, P6, P11, P12; or P1, P2, P7, P4, P9, P6, P10, P11, P12; wherein P1 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), or an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene group, benzofuran, benzothiophene, quinoline, indoline, chroman, quinoxaline, quinazoline group(s) in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4); P6 is d- or l-Bpa, d- or l-Phe$_4$NO$_2$, any amino acid and d- or l-Tyr (e.g., d-Ser-d-Tyr), any amino acid and d- or l-Phe (e.g., d-Ser-d-Phe), and at least three of P7, P8, P9, P10, P11, P12 are basic amino acids with the rest being any amino acid or absent. In various aspects, the amino acid having a simple carbon chain is d- or l-11-aminoundecanoic acid, d- or l-10-aminodecanoic acid, d- or l-9-aminononanoic acid, d- or l-8-aminocaprylic acid, d- or l-7-aminoheptanoic acid, d- or l-6-aminocaproic acid or a similar structure with one or more unsaturated carbon bonds.

In a further embodiment, an invention compound comprises a contiguous peptide or peptidomimetic sequence that includes the following structure: P1, P2, P3, P4, P5, P6, P7, P8, P9, P10, P11, P12; P12, P11, P10, P9, P8, P7, P6, P5, P4, P3, P2, P1; P12, P11, P10, P6, P9, P4, P7, P2, P1; or P1, P2, P7, P4, P9, P6, P10, P11, P12; wherein P1 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4); P6 is d- or l-Bpa, d- or l-Phe$_4$NO$_2$, any amino acid and d- or l-Tyr (e.g., d-Ser-d-Tyr), any amino acid and d- or l-Phe (e.g., d-Ser-d-Phe), any amino acid, or nothing; and at least three of P7, P8, P9, P10, P11, P12 are basic amino acids with the rest being any amino acid or absent. In various aspects, the amino acid having a simple carbon chain is d- or l-aminoundecanoic acid or d- or l-8-aminocaprylic acid.

In yet another embodiment, an invention compound comprises a contiguous peptide or peptidomimetic sequence that includes the following structure: P1, P2, P3, P4, P5, P6 or P6, P5, P4, P3, P2, P1; wherein P1 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, d- or l-Tyr, or d- or l-Phe; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, d- or l-Tyr, or d- or l-Phe; P3 is d- or l-serine, d- or l-arginine, d- or l-cysteine, d- or l-proline, or d- or l-asparagine; P4 is d- or l-tryptophan; and P5 is d- or l-serine, d- or l-arginine, or d- or l-asparagine; or P3, P4, P5 is a single d- or l-aminoundecanoic acid or a single d- or l-8-aminocaprylic acid; P6 is d- or l-Bpa, d- or l-Phe$_4$NO$_2$, (d-Ser-d-Tyr), or (d-Ser-d-Phe).

In still another embodiment, an invention compound comprises a contiguous peptide or peptidomimetic sequence that includes the following structure: P1, P2, P3, P4, P5, P6, P7, P8, P9, P10, P11, P12; P1, P2, P3, P4, P5, P6, P12, P11, P10, P9, P8, P7; P6, P5, P4, P3, P2, P1, P7, P8, P9, P10, P11, P12; P6, P5, P4, P3, P2, P1, P12, P11, P10, P9, P8, P7; P7, P8, P9, P10, P11, P12, P1, P2, P3, P4, P5, P6; P7, P8, P9, P10, P11, P12, P6, P5, P4, P3, P2, P1; P12, P11, P10, P9, P8, P7, P1, P2, P3, P4, P5, P6; P12, P11, P10, P9, P8, P7, P6, P5, P4, P3, P2, P1; P12, P11, P6, P9, P8, P7, P2, P1); P12, P11, P10, P6, P9, P4, P7, P2, P1; P1, P2, P7, P8, P9, P6, P11, P12; or P1, P2, P7, P4, P9, P6, P10, P11, P12; wherein P1 is d- or l-Cha, Nal(2), d- or l-(Phe-2,3,4,5,6-F), d- or l-(Phe-3,4,5F), d- or l-(Phe-4CF3), d- or l-Bpa, d- or l-Phe$_4$NO$_2$, d- or l-Tyr, or d- or l-Phe; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe$_4$NO$_2$, d- or l-Tyr, or d- or l-Phe; P3 is d- or l-serine, d- or l-arginine, d- or l-cysteine, d- or l-proline, or d- or l-asparagine; P4 is d- or l-tryptophan; P5 is d- or l-serine, d- or l-arginine, or d- or l-asparagine; or P3, P4, P5 is a single d- or l-aminoundecanoic acid or a single d- or l-8-aminocaprylic acid; P6 is d- or l-Bpa, d- or l-Phe$_4$NO$_2$, (d-Ser-d-Tyr), or (d-Ser-d-Phe); and at least three of P7, P8, P9, P10, P11, P12 are d- or l-Arg or d- or l-Lys with the rest being any amino acid or absent.

In an additional embodiment, an invention compound comprises a contiguous peptide or peptidomimetic sequence that includes the following structure: P1, P2, P3, P4, P5, P6, P7, P8, P9, P10, P11, P12; P12, P11, P10, P9, P8, P7, P6, P5, P4, P3, P2, P1; P12, P11, P10, P6, P9, P4, P7, P2, P1; or P1, P2, P7, P4, P9, P6, P10, P11, P12; wherein P1 is d- or l-Cha, or d- or l-Nal(2); P2 is d- or l-(Phe-2,3,4,5,6-F), d- or l-(Phe-3,4,5F), d- or l-(Phe-4CF3); and at least three of P7, P8, P9, P10, P11, P12 are d- or l-Arg with the rest being any amino acid or absent; P3 is d- or l-serine; P4 is d- or l-tryptophan; P5 is d- or l-serine or d- or l-asparagine; P6 is d- or l-Bpa, d- or l-Phe$_4$NO$_2$, (d- or l-Ser or d- or l-Tyr), or (d- or l-Ser or d- or l-Phe).

In yet an additional embodiment, an invention compound comprises a contiguous peptide or peptidomimetic sequence that includes the following structure: P1, P2, P3, P4, P5, P6 or P6, P5, P4, P3, P2, P1; wherein P1 is d- or l-Cha, or d- or l-Nal(2); P2 is (d- or l-Phe-2,3,4,5,6-F), (d- or l-Phe-3,4,5F) or (d- or l-Phe-4CF3); P3 is d- or l-Ser; P4 is d- or l-Trp; P5 is d- or l-Ser; P6 is d- or l-Bpa, or (d- or l-Ser or d- or l-Tyr).

In a further embodiment, an invention compound comprises a contiguous peptide or peptidomimetic sequence that includes the following structure: P1, P2, P3, P4, P5, P6; P6, P5, P4, P3, P2, P1; P1, P2, P3, P4, P5, P6, P7, P8, P9, P10, P11, P12; P1, P2, P3, P4, P5, P6, P12, P11, P10, P9, P8, P7; P6, P5, P4, P3, P2, P1, P7, P8, P9, P10, P11, P12; P6, P5, P4, P3, P2, P1, P12, P11, P10, P9, P8, P7; P7, P8, P9, P10, P11, P12, P1, P2, P3, P4, P5, P6; P7, P8, P9, P10, P11, P12, P6, P5, P4, P3, P2, P1; P12, P11, P10, P9, P8, P7, P1, P2, P3, P4, P5, P6; P12, P11, P10, P9, P8, P7, P6, P5, P4, P3, P2, P1; P12, P11, P6, P9, P8, P7, P2, P1; P12, P11, P10, P6, P9, P4, P7, P2, P1; P1, P2, P7, P8, P9, P6, P11, P12; or P1, P2, P7, P4, P9, P6, P10, P11, P12; wherein P1 is d- or l-Cha, or d- or l-Nal(2); P2 is (d- or l-Phe-2,3,4,5,6-F), (d- or l-Phe-3,4,5F) or (d- or l-Phe-4CF3); P3 is any amino acid (e.g., d- or l-Ser, or d- or l-Pro); P4 is d- or l-Trp; P5 is any amino acid (e.g., d- or l-Ser); P7 is d- or l-Arg; P8 is d- or l-Arg; P9 is d- or l-Arg; P10 is d- or l-Gln or d- or l-Arg; P11 is d- or l-Arg; P12 is d- or l-Arg; P6 is d- or l-Bpa or (d- or l-Ser or d- or l-Tyr).

In still another embodiment, an invention compound comprises a contiguous peptide or peptidomimetic sequence that includes the following structure: P1, P2, P3, P4, P5, P6, P7, P8, P9, P10, P11, P12; P12, P11, P10, P9, P8, P7, P6, P5, P4, P3, P2, P1; P12, P11, P10, P6, P9, P4, P7, P2, P1; or P1, P2, P7, P4, P9, P6, P10, P11, P12; wherein P1 is d- or l-Cha or d- or l-Nal(2); P2 is (d- or l-Phe-2,3,4,5,6-F); P3 is d- or l-Ser; P4 is d- or l-Trp; P5 is d- or l-Ser; P7 is d- or l-Arg; P8 is d- or l-Arg; P9 is d- or l-Arg; P10 is d- or l-Gln or d- or l-Arg; P11 is d- or l-Arg; P12 is d- or l-Arg; P6 is d- or l-Bpa or (d- or l-Ser or d- or l-Tyr).

In still further embodiments, an invention compound comprises a contiguous peptide or peptidomimetic sequence that includes the following structure: (d-Bpa) (d-Ser)(d-Trp) (d-Ser) (d-Phe-2,3,4,5,6-F) (d-Cha)(d-Arg) (d-Arg) (d-Arg) (d-Gln)(d-Arg) (d-Arg); (d-Arg) (d-Arg) (d-Arg) (d-Gln)(d-Arg) (d-Arg) (d-Bpa)(d-Ser)(d-Trp)(d-Ser) (d-Phe-2,3,4,5,6-F) (d-Cha); (d-Bpa) (d-Ser)(d-Trp)(d-Ser) (d-Phe-2,3,4,5,6-F)(d-Cha)(d-Arg) (d-Arg) (d-Gln) (d-Arg) (d-Arg) (d-Arg); (d-Arg) (d-Arg) (d-Gln) (d-Arg) (d-Arg) (d-Arg) (d-Bpa) (d-Ser)(d-Trp)(d-Ser) (d-Phe-2,3,4,5,6-F) (d-Cha); (d-Cha) (d-Phe-2,3,4,5,6-F) (d-Ser)(d-Trp)(d-Ser) (d-Bpa) (d-Arg) (d-Arg) (d-Arg) (d-Gln)(d-Arg) (d-Arg); (d-Arg) (d-Arg) (d-Gln)(d-Arg) (d-Arg) (d-Cha) (d-Phe-2,3,4,5,6-F) (d-Ser)(d-Trp)(d-Ser) (d-Bpa); (d-Cha) (d-Phe-2,3,4,5,6-F) (d-Ser) (d-Trp) (d-Ser) (d-Bpa) (d-Arg) (d-Arg) (d-Gln) (d-Arg) (d-Arg) (d-Arg); (d-Arg) (d-Arg) (d-Gln) (d-Arg) (d-Arg) (d-Arg) (d-Cha) (d-Phe-2,3,4,5,6-F) (d-Ser) (d-Trp)(d-Ser) (d-Bpa); (d-Arg) (d-Arg) (d-Arg) (d-Arg) (d-Arg) (d-Arg) (d-Cha) (d-Phe-2,3,4,5,6-F) (d-Ser) (d-Trp) (d-Ser) (d-Bpa); (d-Cha) (d-Phe-2,3,4,5,6-F) (d-Ser)(d-Trp) (d-Ser) (d-Bpa) (d-Arg) (d-Arg) (d-Arg) (d-Arg) (d-Arg) (d-Arg); (d-Arg) (d-Arg) (d-Arg) (d-Arg) (d-Arg) (d-Arg) (d-Bpa) (d-Ser)(d-Trp)(d-Ser) (d-Phe-2,3,4,5,6-F)(d-Cha); (d-Bpa) (d-Ser)(d-Trp)(d-Ser) (d-Phe-2,3,4,5,6-F)(d-Cha) (d-Arg) (d-Arg) (d-Arg) (d-Arg) (d-Arg) (d-Arg); (d-Arg) (d-Arg) (d-Bpa) (d-Arg) (d-Arg) (d-Arg) (d-Phe-2,3,4,5,6-F)(d-Cha); (d-Cha) (d-Phe-2,3,4,5,6-F) (d-Arg) (d-Arg) (d-Arg) (d-Bpa) (d-Arg)(d-Arg); (d-Arg) (d-Arg) (d-Arg) (d-Bpa) (d-Arg) (d-Trp) (d-Arg) (d-Phe-2,3,4,5,6-F)(d-Cha); (d-Cha) (d-Phe-2,3,4,5,6-F) (d-Arg)(d-Trp) (d-Arg) (d-Bpa) (d-Arg) (d-Arg) (d-Arg); (d-Arg) (d-Arg) (d-Arg) (d-Bpa) (d-Arg)(d-Trp) (d-Arg) (d-Phe-2,3,4,5,6-F)(d-Cha); (d-Cha) (d-Phe-2,3,4,5,6-F) (d-Arg)(d-Trp) (d-Arg) (d-Bpa) (d-Arg) (d-Arg) (d-Arg); (d-Arg) (d-Arg) (d-Arg) (d-Arg) (d-Arg) (d-Arg)(d-Bpa)(d-Arg)(d-Arg) (d-Arg) (d-Phe-2,3,4,5,6-F)(d-Cha); or (d-Cha) (d-Phe-2,3,4,5,6-F) (d-Arg) (d-Arg) (d-Arg) (d-Bpa) (d-Arg)(d-Arg)(d-Arg).

In still additional embodiments, an invention compound comprises a contiguous peptide or peptidomimetic sequence that includes the following structure: (d-Bpa)(d-Ser)(d-Trp) (d-Ser)(d-Phe-2,3,4,5,6-F)(d-Cha)(d-Arg)(d-Arg)(d-Arg)(d-Gln) (d-Arg)(d-Arg).

In further embodiments, an invention compound comprises a contiguous peptide or peptidomimetic sequence: $X_1$ $X_2$ $X_3$ $X_4$ $X_5$ $X_6$ $X_7$ $X_8$ $X_9$ $X_{10}$ $X_{11}$, wherein X1 is L, F, W, M, R, I, V, Y, K, or absent, X2 is Y, F, A, W, S or T, X3 is any amino acid, X4 is any amino acid, X5 is any amino acid, X6 is S, A, N, H or P, X7 is any amino acid, X8 is any amino acid, X9 is any amino acid or absent, X10 is N, G, L, S, M, P, N, A or absent, and X11 is L or absent. In various aspects, $X_1$ is L, F, W, M, R or absent or $X_1$ is L, F or W; $X_2$ is Y, F, A; $X_3$ is R, T, S, H, D, G, A, L, K, A, N, Q or P, or, $X_3$ is R, T, S, H, D, G, A or L, or, $X_3$ is R, T, S or H; $X_4$ is S, T, G, A, L, R, I, M, V, P, or, $X_4$ is S, T, G, A, L, R, or, $X_4$ is S; $X_5$ is P, A, G, S or T, or, $X_5$ is P; $X_6$ is S, N, H, P, A, G or T, or, $X_6$ is S; $X_7$ is M, F, Y, D, E, N, Q, H, G, I, L, V, A, P, N or W, or, $X_7$ is M, F, Y, D, E, N, Q or H, or, $X_7$ is M, F, Y, Q or H; $X_8$ is P, F, Y, W, L, G, M, D, E, N, Q, H, I, V, A or P, or, $X_8$ is P, F, Y or W, or, $X_8$ is Y; $X_9$ is E, G, L, S, M, P, N, D, A, T, P or absent; $X_{10}$ is absent; $X_{11}$ is absent. In still further embodiments, $X_2$ is Y, $X_5$ is P, and $X_{10}$ is N; $X_3$ is R, $X_8$ is P, and $X_{11}$ is L; and $X_4$ is S, $X_5$ is P, $X_6$ is S, $X_9$ is E, $X_{10}$ is N and $X_{11}$ is L.

In further embodiments, an invention compound comprises a contiguous peptide or peptidomimetic sequence:

```
Y G G P G G G G N;          (SEQ ID NO: 1)

R Y S L P P B L S N M;      (SEQ ID NO: 2)

L A R S A S M P E A L;      (SEQ ID NO: 3)

L Y R S P S M P E N L;      (SEQ ID NO: 4)

L Y R S P A M P E N L;      (SEQ ID NO: 5)

W Y R S P S F Y E N L;      (SEQ ID NO: 6)

W Y R S P S Y Y E N L;      (SEQ ID NO: 7)

or,

W Y R S P S Y Y.            (SEQ ID NO: 8)
```

In alternative embodiments, an invention compound comprises a contiguous peptide or peptidomimetic sequence:

```
L Y R S P S Y P E N L,      (SEQ ID NO: 9)

L Y R S P S Y F E N L,      (SEQ ID NO: 10)

L Y R S P S Y Y E N L,      (SEQ ID NO: 11)

L Y R S P S Y W E N L,      (SEQ ID NO: 12)

L Y R S P S N P E N L,      (SEQ ID NO: 13)

L Y R S P S N F E N L,      (SEQ ID NO: 14)

L Y R S P S N Y E N L,      (SEQ ID NO: 15)

L Y R S P S N W E N L,      (SEQ ID NO: 16)

L Y R S P S H P E N L,      (SEQ ID NO: 17)

L Y R S P S H F E N L,      (SEQ ID NO: 18)

L Y R S P S H Y E N L,      (SEQ ID NO: 19)

L Y R S P S H W E N L,      (SEQ ID NO: 20)

L Y S S P S M P E N L,      (SEQ ID NO: 21)

L Y S S P S M F E N L,      (SEQ ID NO: 22)

L Y S S P S M Y E N L,      (SEQ ID NO: 23)

L Y S S P S M W E N L,      (SEQ ID NO: 24)

L Y S S P S F P E N L,      (SEQ ID NO: 25)

L Y S S P S F P E N L,      (SEQ ID NO: 26)

L Y S S P S F F E N L,      (SEQ ID NO: 27)

L Y S S P S F Y E N L,      (SEQ ID NO: 28)

L Y S S P S F W E N L,      (SEQ ID NO: 29)

L Y S S P S Y P E N L,      (SEQ ID NO: 30)

L Y S S P S Y F E N L,      (SEQ ID NO: 31)
```

LYSSPSYYENL, (SEQ ID NO: 32)
LYSSPSYWENL, (SEQ ID NO: 33)
LYSSPSQPENL, (SEQ ID NO: 34)
LYSSPSQWENL, (SEQ ID NO: 35)
LYSSPSHPENL, (SEQ ID NO: 36)
LYSSPSHFENL, (SEQ ID NO: 37)
LYSSPSHYENL, (SEQ ID NO: 38)
LYSSPSHWENL, (SEQ ID NO: 39)
LYTSPSMPENL, (SEQ ID NO: 40)
LYTSPSMFENL, (SEQ ID NO: 41)
LYTSPSMYENL, (SEQ ID NO: 42)
LYTSPSMWENL, (SEQ ID NO: 43)
LYTSPSFPENL, (SEQ ID NO: 44)
LYTSPSFFENL, (SEQ ID NO: 45)
LYTSPSFYENL, (SEQ ID NO: 46)
LYTSPSFWENL, (SEQ ID NO: 47)
LYTSPSYPENL, (SEQ ID NO: 48)
LYTSPSYFENL, (SEQ ID NO: 49)
LYTSPSYYENL, (SEQ ID NO: 50)
LYTSPSYWENL, (SEQ ID NO: 51)
LYTSPSNPENL, (SEQ ID NO: 52)
LYTSPSNFENL, (SEQ ID NO: 53)
LYTSPSNYENL, (SEQ ID NO: 54)
LYTSPSNWENL, (SEQ ID NO: 55)
LYTSPSHPENL, (SEQ ID NO: 56)
LYTSPSHFENL, (SEQ ID NO: 57)
LYTSPSHYENL, (SEQ ID NO: 58)
LYTSPSHWENL, (SEQ ID NO: 59)
LYHSPSYPENL, (SEQ ID NO: 60)
LYHSPSYFENL, (SEQ ID NO: 61)
LYHSPSYYENL, (SEQ ID NO: 62)
LYHSPSYWENL, (SEQ ID NO: 63)
LFTSPSYPENL, (SEQ ID NO: 64)
LFTSPSYFENL, (SEQ ID NO: 65)
LFTSPSYYENL, (SEQ ID NO: 66)
LFTSPSYWENL, (SEQ ID NO: 67)
FYSSPSHPENL, (SEQ ID NO: 68)
FYSSPSHFENL, (SEQ ID NO: 69)
FYSSPSHYENL, (SEQ ID NO: 70)
FYSSPSHWENL, (SEQ ID NO: 71)
FYTSPSMPENL, (SEQ ID NO: 72)
FYTSPSMFENL, (SEQ ID NO: 73)
FYTSPSMYENL, (SEQ ID NO: 74)
FYTSPSMWENL, (SEQ ID NO: 75)
FYTSPSFPENL, (SEQ ID NO: 76)
FYTSPSFFENL, (SEQ ID NO: 77)
FYTSPSFYENL, (SEQ ID NO: 78)
FYTSPSFWENL, (SEQ ID NO: 79)
FYTSPSYPENL, (SEQ ID NO: 80)
FYTSPSYFENL, (SEQ ID NO: 81)
FYTSPSYYENL, (SEQ ID NO: 82)
FYTSPSYWENL, (SEQ ID NO: 83)
WYRSPSMPENL, (SEQ ID NO: 84)
WYRSPSMFENL, (SEQ ID NO: 85)
WYRSPSMYENL, (SEQ ID NO: 86)
WYRSPSMWENL, (SEQ ID NO: 87)
WYRSPSFPENL, (SEQ ID NO: 88)
WYRSPSFFENL, (SEQ ID NO: 89)
WYRSPSFYENL, (SEQ ID NO: 90)
WYRSPSFWENL, (SEQ ID NO: 91)
WYRSPSYPENL, (SEQ ID NO: 92)
WYRSPSYFENL, (SEQ ID NO: 93)
WYRSPSYYENL, (SEQ ID NO: 94)
WYRSPSYWENL, (SEQ ID NO: 95)
WYTSPSMPENL, (SEQ ID NO: 96)
WYTSPSMFENL, (SEQ ID NO: 97)
WYTSPSMYENL, (SEQ ID NO: 98)
WYTSPSMWENL, (SEQ ID NO: 99)
WYTSPSFPENL, (SEQ ID NO: 100)
WYTSPSFFENL, (SEQ ID NO: 101)
WYTSPSFYENL, (SEQ ID NO: 102)
WYTSPSFWENL, (SEQ ID NO: 103)
WYTSPSYPENL, (SEQ ID NO: 104)
WYTSPSYFENL, (SEQ ID NO: 105)
WYTSPSYYENL, (SEQ ID NO: 106)
WYTSPSYWENL, (SEQ ID NO: 107)
WYTSPSHPENL, (SEQ ID NO: 108)
WYTSPSHFENL, (SEQ ID NO: 109)
WYTSPSHYENL, (SEQ ID NO: 110)
WYTSPSHWENL, (SEQ ID NO: 111)

```
-continued
L K R S P S M P E N L,    (SEQ ID NO: 112)

L Y I S P S M P E N L,    (SEQ ID NO: 113)

or

L Y R S P S M V E N L.    (SEQ ID NO: 114)
```

Invention compounds optionally include a cell membrane permeant. The cell membrane permeant can comprise a polypeptide, such as a TAT protein transduction domain, e.g., a sequence Y G R K K R R Q R R R (SEQ ID NO: 115).

The invention compounds include prodrugs. As used herein, a "prodrug" is a compound that is metabolized, converted or modified to an active form, e.g., a peptide of peptidomimetic having anti-fungal activity or function, in vivo. Prodrugs are often useful because they may be easier to administer than the parent drug or exhibit increased bioavailabilty or solubility as compared to the parent drug. A particular non-limiting example of a prodrug is a polypeptide which is bonded through an amino- or a carboxy-terminal group to an invention peptide or peptidomimetic. The polypeptide hydrolyzes or is metabolized in vivo to release the active peptide or peptidomimetic. The invention compounds and methods therefore include prodrugs of peptides and peptidomimetics that are metabolized, converted or modified in vivo to an active form of the peptide or peptidomimetic.

Invention compounds have anti-fungal activity or anti-fungal function or G2 abrogating or G2 inhibiting activity. As used herein, the terms "anti-fungal activity" and "anti-fungal function" mean any detectable or measurable decrease, reduction or inhibition of fungal contact, contamination, growth, viability, proliferation or infection in vitro, ex vivo, in vivo, in the environment, in an agricultural or horticultural setting, or in a commercial, industrial, residential or community setting. A compound that is a fungicide typically kills fungus and a compound that is a fungistat typically reduces or inhibits growth, viability or proliferation.

A decrease, reduction or inhibition of fungal contact, contamination, growth, viability, proliferation or infection can reduce the amount of fungal contamination, growth, viability, proliferation or infection; or prevent or inhibit progression or a worsening of an acute or chronic symptom, condition or disorder associated with fungal contact, growth, contamination, infection or proliferation. For example, in an animal, one or more symptoms or conditions associated with or caused by a fungal infection that can be reduced or inhibited include irritation, itching, inflammation, burning, hives, weeping, pruritus, excess discharge, discoloration, headache, and fatigue. In the environment, or in an agricultural, horticultural, industrial, community, commercial or residential setting, a decrease, reduction or inhibition of fungal contact, contamination, growth, viability, proliferation or infection can reduce the amount of fungal contact, contamination, growth or proliferation.

Anti-fungal activity and anti-fungal function can include a decrease or reduction in susceptibility to fungal contact, contamination, growth, viability, proliferation or infection, or a decrease or reduction in a recurrence of fungal contact, contamination, growth or infection. Anti-fungal activity and anti-fungal function may occur in a any living organism or non-living object, e.g., a mammal such as a human or vetirinary subject, or in an inorganic or organic material susceptible to fungal contamination, growth or infection, such as living or dead organic matter, biological fluids, cells, organs or tissues, or any plant, tree, bush or horticultural or agricultural product (e.g. flowers, grass, wood, nuts, produce, grain, etc.), whether in the environment, or in an industrial, commercial, residential, community or agricultural or horticultural setting.

As used herein, the term "object" generally refers to a non-living or formerly living physical entity. Objects may be composed of organic or inorganic material, or combinations thereof. Non-living organisms are within the meaning of the term object, as used herein. Objects susceptible to fungal contact, contamination, growth, proliferation or infection include machinery, instruments, appratus, devices, tools, equipment (e.g., for food processing), containers, packaging materials or surfaces. Objects further include medical materials found in health care facilities, such as clinics and hospitals. Objects susceptible to fungal contact, contamination, growth, proliferation and infection further include, for example, cloth, leather, shoes, socks, gloves, hats, carpet and rugs, floors, wood, wallboard and household dust. Essdentially anything that is made of organic material is susceptible to fungal contact, contamination, growth, proliferation and infection.

The term "fungus" and grammatical variations thereof means any organism within the fungus kingdom. Particular examples include yeast, mold, slime, mushroom and lichen.

As used herein, the terms "G2" and "G2/M" refer to the cell cycle G2 to M phase checkpoint. The terms "G2 abrogating" and "G2 inhibiting" activity mean that the G2 checkpoint of the cell cycle is disrupted such that the cell progresses to M phase without a G2 checkpoint, or the G2 checkpoint has a shorter duration of time as compared to the amount of time that the cell would normally be in G2. Thus, for example, a peptide or peptidomimetic that abrogates or inhibits G2 checkpoint will accelerate the G2 to M phase transition, which can in turn induce or stimulate cell death before or after cells enter M phase. Compounds that abrogate or inhibit G2 checkpoint refer to any compound producing a detectable or measurable reduction in the amount of time that the cell is in the G2 checkpoint.

As used herein, the terms "peptide," "polypeptide" and "protein" are used interchangeably and refer to two or more amino acids covalently linked by an amide bond or non-amide equivalent. The peptides of the invention can be of any length. The peptides can have from about 5 to 100 or more residues, such as, 5 to 12, 12 to 15, 15 to 18, 18 to 25, 25 to 50, 50 to 75, 75 to 100, or more in length. Peptides having as few as five residues have activity. For example, (Bpa)(X)(Trp)(X)(Bpa) has approximately the same activity as (Bpa)(X)(Trp)(X)(PheF5)(Cha). The peptides of the invention include l- and d-isomers, and combinations of l- and d-isomers. The peptides can include modifications typically associated with post-translational processing of proteins, for example, cyclization (e.g., disulfide or amide bond), phosphorylation, glycosylation, carboxylation, ubiquitination, myristylation, or lipidation.

Peptides disclosed herein further include compounds having amino acid structural and functional analogues, for example, peptidomimetics having synthetic or non-natural amino acids or amino acid analogues, so long as the mimetic has one or more functions or activities, e.g., anti-fungal activity. The compounds of the invention therefore include "mimetic" and "peptidomimetic" forms.

As used herein, the terms "mimetic" and "peptidomimetic" refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the mimetic's activity. Routine testing can be used to determine whether a mimetic has the requisite activity, e.g., that it has detectable anti-fungal activity. The phrase "substantially the same," when used in reference to a mimetic or peptidomimetic, means that the mimetic or peptidomimetic has one or more activities or functions of the referenced molecule, e.g., anti-fungal activity Peptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267–357, "Peptide and Backbone Modifications," Marcel Decker, NY).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalnine; D- or L-p-biphenylphenylalanine; K- or L-p-methoxy-biphenylphenylalanine; D- or L-2-indole(alkyl)alanines; and D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic rings include, for example, thiazolyl, thiophenyl, pyrazolyl, benzimidazolyl, naphthyl, furanyl, pyrrolyl, and pyridyl aromatic rings.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N=C=N—R') including, for example, 1-cyclohexyl-3(2-morpholinyl-(4-ethyl) carbodiimide or 1-ethyl-3(4-azonia-4,4-dimetholpentyl) carbodiimide. Aspartyl or glutamyl groups can also be converted to asparaginyl and glutaminyl groups by reaction with ammonium ions.

Mimetics of basic amino acids can be generated by substitution, for example, in addition to lysine and arginine, with the amino acids ornithine, citrulline, or (guanidino)-acetic acid, or (guanidino)alkyl-acetic acid, where alkyl can be substituted or unsubstituted methyl, ethyl, propyl, hexyl, butyl, pentyl, isopropyl, iso-butyl, sec-isotyl, iso-pentyl, or a non-acidic amino acid. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine mimetics can be generated by reacting arginyl with one or more reagents including, for example, phenylglyoxal, 2,3-butanedione, 1,2-cyclohexanedione, or ninhydrin, optionally under alkaline conditions. Tyrosine residue mimetics can be generated by reacting tyrosyl with aromatic diazonium compounds or tetranitromethane. N-acetylimidizol and tetranitromethane can be used to form O-acetyl tyrosyl species and 3-nitro derivatives, respectively.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, 3- or 4-hydroxy proline, dehydroproline, 3- or 4-methylproline, and 3,3,-dimethylproline. Histidine mimetics can be generated by reacting histidyl with diethylprocarbonate or para-bromophenacyl bromide. Other mimetics include, for example, those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D- amino acid, but which can additionally be referred to as the R- or S-form.

Invention peptides and peptidomimetics further include modified forms of the sequences set forth herein, provided that the modified form retains, at least a part of, the function of the unmodified or reference peptide or peptidomimetic. For example, a modified peptide or peptidomimetic will retain at least a part of anti-fungal activity, but may have increased or decreased anti-fungal activity or G2 abrogating activity relative to a reference peptide or peptidomimetic.

Modified peptides and peptidomimetics can have one or more amino acid residues substituted with another residue, added to the sequence or deleted from the sequence. In one embodiment, the modified peptide or peptidomimetic has one or more amino acid substitutions, additions or deletions (e.g., 1-3, 3-5, 5-10 or more residues). In one aspect, the substitution is with an amino acid or mimetic whose side chain occupies a similar space with the reference amino acid or mimetic (the amino acid or mimetic that is being substituted). In still another aspect, the substitution is with a non-human amino acid which is structurally similar to the human residue. In a particular aspect, the substitution is a conservative amino acid substitution.

As used herein, the term "similar space" means a chemical moiety that occupies a three-dimensional space similar in size to a reference moiety. Typically, a moiety that occupies a similar space will be similar in size to the reference moiety. An amino acid or mimetic that "occupies a similar side chain space" has a side chain that occupies a three-dimensional space similar in size to the reference amino acid or mimetic. Specific examples for d-(Phe-2,3,4,5,6-F), l-(Phe-2,3,4,5,6-F), d-(Phe-3,4,5F), l-(Phe-3,4,5F), d-(Phe-4CF3) or l-(Phe-4CF3), are (1 or d-Phe-2R1,3R2,4R3,5R4,6R5) where R1,R2,R3,R4,R5 can be chloride, bromide, fluoride, iodide, hydrogen, hydrogen oxide or absent. For small molecules, e.g., fluoride which has a size of about 1 Angstrom, similar space may be absence of a moiety.

The term "conservative substitution" means the replacement of one amino acid by a biologically, chemically or structurally similar residue. Biologically similar means that the substitution is compatible with biological activity, e.g., an anti-fungal activity. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Invention peptides and peptidomimetics therefore include peptides and peptidomimetics having a sequence that is not identical to peptide and peptidomimetic sequences set forth in Table 1 and exemplified herein. In one embodiment, a peptide or peptidomimetic has a sequence with 50%, 60%, 70%, 75%, 80%, 85%, 90%, 95%, or more identity to a sequence set forth herein.

Invention peptides and peptidomimetics include peptides and peptidomimetics that are substantially identical to a sequence set forth herein. The term "substantially identical," when used in reference to a peptide or peptidomimetic, means that the sequence has at least 75% or more identity to a reference sequence (e.g., 80%, 85%, 90%, 95%, 96%, 97%, 98%, 99%). The length of comparison sequences will generally be at least 5 amino acids, but typically more, at least 6–10, 10 to 15 or more residues. In one aspect, the identity is over a defined sequence region, e.g., the amino or carboxy terminal 3–5 residues.

The compounds of the invention, including peptides and peptidomimetics can be produced and isolated using any method known in the art. Peptides can be synthesized, whole or in part, using chemical methods known in the art (see, e.g., Caruthers (1980) Nucleic Acids Res. Symp. Ser. 215–223; Horn (1980) Nucleic Acids Res. Symp. Ser. 225–232; and Banga, A. K., Therapeutic Peptides and Proteins, Formulation, Processing and Delivery Systems (1995) Technomic Publishing Co., Lancaster, Pa.). Peptide synthesis can be performed using various solid-phase techniques (see, e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the manufacturer's instructions.

Individual synthetic residues and polypeptides incorporating mimetics can be synthesized using a variety of procedures and methodologies known in the art (see, e.g., Organic Syntheses Collective Volumes, Gilman, et al. (Eds) John Wiley & Sons, Inc., NY). Peptides and peptide mimetics can also be synthesized using combinatorial methodologies. Techniques for generating peptide and peptidomimetic libraries are well known, and include, for example, multipin, tea bag, and split-couple-mix techniques (ses, for example, al-Obeidi (1998) Mol. Biotechnol. 9:205–223; Hruby (1997) Curr. Opin. Chem. Biol. 1:114–119; Ostergaard (1997) Mol. Divers. 3:17–27; and Ostresh (1996) Methods Enzymol. 267:220–234). Modified peptides can be further produced by chemical modification methods (see, for example, Belousov (1997) Nucleic Acids Res. 25:3440–3444; Frenkel (1995) Free Radic. Biol. Med. 19:373–380; and Blommers (1994) Biochemistry 33:7886–7896).

Invention compounds and combination compositions are useful for inhibiting fungal contact, contamination, growth, viability, proliferation or infection in vitro, ex vivo and in vivo (e.g., systemically, regionally, topically or on a mucosal tissue). As such, any living or non-living thing having or at risk of having fungal contact, contamination, growth, viability, proliferation or infection, or damage or a condition caused by or associated with fungal contact, contamination, growth, viability, proliferation or infection, can be treated with an invention compound.

Thus, in accordance with the invention, there are provided methods for inhibiting, decreasing and reducing fungal contact, contamination, growth, viability, proliferation and infection, in vitro, ex vivo and in vivo. Such methods include inhibiting, decreasing or reducing contact with a fungus; inhibiting, decreasing or reducing growth or proliferation of a fungus; inhibiting, decreasing or reducing infection by a fungus; inhibiting, decreasing or reducing contamination by a fungus; inhibiting, decreasing or reducing viability of a fungus; and inhibiting, decreasing or reducing susceptibility to or recurrence of fungal contact, contamination, growth, viability, proliferation or infection.

In one embodiment, a method includes contacting a living organism or non-living object (e.g., any material) with an amount of an invention compound sufficient to decrease, reduce or inhibit fungal contact, contamination, growth, viability, proliferation or infection of the organism, object or objects in close proximity to the object. In one aspect, the organism is an animal, such as a mammal (e.g., a human). In another aspect, the object comprises an organic or inorganic material (e.g., a construction material or medical material). In yet another aspect, the object comprises an instrument, machinery, equipment, device, tool, medical material, or surface. In various additional aspects, the object is present in the environment or in an industrial, residential, commercial, community, agricultural or horticultural setting.

As used herein, the term "object" means any non-living or formerly living physical entity that can be in contact with or contaminated with a fungus, infected with a fungus, or that allows, supports or facilitates fuingal contact, contamination, growth, viability, proliferation or infection. Objects therefore include any organic or inorganic material susceptible to fungal contact, contamination, growth or infection, such as non-living organic matter, biological fluids, cells, organs or tissues, or parts of formerly lving organisms, such as a horticultural or agricultural product (e.g. plants, grass and flowers, vegetables, fruits, nuts and grains, parts thereof, etc.). An organism refers to any living thing, e.g., a mammal such as a human or veterinary subject, a plant, grass, tree, bush, plant, vegetable, fruit etc. Plant parts include leaves, stems, roots, flowers, seeds, trunks and branches because fungal growth, contamination or infection can be present at least in part on a leaf, stem, root, flower, seed, trunk or branch.

Objects further include any apparatus, instrument, device, tool, machinery, equipment (e.g., for food processing), container, packaging material or surface. The object may be present in a residential, commercial or community setting, such as a house, apartment, condominium, hotel or motel, hospital or clinic, school, auditorium or office that contains surfaces or materials such as wood, fiber or other organic or inorganic material, or a ventilation system, susceptible to fungal contact. Objects may be present in an industrial setting (e.g., where food such as cheese, milk, or any beverage or food product, unprocessed, aged, cultured, processed or fermented, is manufactured, processed, distributed, stored, or sold), for example, a manufacturing, processing, storage or distribution building or facility that contains, for example, machinery or equipment, or organic matter (e.g., food or beverages), susceptible to fungal contact, contamination, growth, viability, proliferation or infection. The object may be present in the environment, such as a farm or ranch, or in an agricultural or horticultural setting (e.g., a greenhouse or nusery), or other area where harvesting or cultivation occurs. The object may also be present in the natural environment, for example, where logging of trees occurs.

Further provided are methods of treating fungal contact, contamination, growth, proliferation or infection, or an associated disorder in a subject, including conditions caused by or associated with fungal contact, contamination, growth, proliferation or infection, after or prior to (e.g., prophylaxis) the subject being contacted, contaminated or infected. In one embodiment, a method includes administering to a subject having or at risk of having a fungal infection, an amount of an invention compound effective to treat the fungal infection. In one aspect, the amount is sufficient to improve the subject's condition. In additional aspects, the improvement includes a reduction of the severity or duration of one or more symptoms caused by fungal growth or a fungal infection, a reduction or decrease in the subject's susceptibility to fungal growth or a fungal infection, or a reduction or decrease in recurrence of fungal growth or a fungal infection. In yet another aspect, the subject is administered an invention compound prior to, contemporaneously with, or after administering another treatment, e.g., an anti-fungal treatment or an anti-fungal agent. In additional particular aspects, the fungal infection is located in skin (e.g., scalp, underarm, foot, groin), toe or nail, hair or a mucosal tissue (e.g., oral, nasopharyngeal, respiratory, gastric, reproductive or glandular, such as, gastrointestinal tract, mouth, lungs, bronchial passages, nasal passages and sinuses, genitourinary tract, vagina, etc.).

Infections or associated disorders amenable to treatment include any fungal infection or disorder caused by or associated with fungal infection, including prohylaxis (prevention or decreasing the recurrence or susceptibility to fungal contact, contamination, growth, proliferation or infection). Particular non-limiting genera of fungi that may be treated in accordance with the invention include, for example, *Absidia, Acremonium, Actinomadura, Alternaria, Apophysomyces, Arthrinium, Arthrographis, Aspergillus, Aureobasidium, Basidiobolus, Beauveria, Bipolaris, Blastomyces, Blastoschizomyces, Botrytis, Candida* (*C. albicans, C. krusei, C. tropicalis, C. parapsilosis* or *C. glabrata*), *Chaetomium, Chrysosporium, Cladophialophora, Cladosporium, Coccidioides, Conidiobolus, Cryptococcus, Cunninghamella, Curvularia, Dermatophytes, Emmonsia, Epicoccum, Epidermophyton, Exophiala, Fonsecaea, Fusarium, Geotrichum, Gliocladium, Graphium, Helminthosporium, Histoplasma, Hortaea werneckii, Lacazia, Leptosphaeria, Madurella, Malassezia, Malbranchea, Microsporum, Mucor, Neotestudina, Nigrospora, Nocardia, Nocardiopsis, Paecilomyces, Paracoccidioides, Penicillium, Phaeococcomyces, Phialophora, Phoma, Piedraia, Pichia, Pneumocystis, Pseudallescheria, Pyrenochaeta, Rhizomucor, Rhizopus, Rhodotorula, Saccharomyces, Scedosporium, Scopulariopsis, Sepedonium, Sporobolomyces, Sporothrix, Sporotrichum, Stachybotrys, Stemphylium, Streptomyces, Syncephalastrum, Torulopsis, Trichoderma, Trichophyton, Trichosporon, Trichothecium, Ulocladium, Ustilago, Verticillium, Wangiella* and *Zygomycetes*.

Particular non-limiting examples of fungus treatable in accordance with the invention in animals include, for example, dermatophytes which causes ringworm, onychomycosis, Jock-itch and athlete's foot; paracoccidioidomycosis; blastomycosis; mucormycosis; cryptococcosis; *Coccidioides immitis*, which causes coccidioidomycosis; *Histoplasma capsulatum* which causes histoplasmosis; *Candida albicans* which causes candidiasis; and *Aspergillus fumigatus* which causes aspergillosis. Particular applications for the compounds of the invention include skin (e.g., scalp, underarm, foot, groin), mucosa (oral, nasopharyngeal, respiratory, gastric, reproductive, glandular, such as gastrointestinal tract, mouth, bronchial tubes, lung, nasal passages and sinuses, vagina, etc.), hair, nail and toe treatments.

Particular non-limiting examples of fungus treatable in accordance with the invention in an agricultural or horticultural setting include, for example, black spot, glomerella, ripe spot, sooty blotch, septoria leaf spot, cercospora leaf spot, rust, downy mildew, brown rot, brown patch, smuts, verrucosisl, dead arm disease, mycosphaerella leaf spot, black spot (roses), flower blight, septoria leaf blight, early and late blight, leaf mould, anthracnose, ring spot, dollar spot, northern leaf blight, alternaria and leaspora spot.

Particular non-limiting examples of molds (fungus) in industrial, commercial and residential settings include, for example, *Stachybotrys chartarum* (*Stachybotrys atra*), which causes animal and human mycotoxicosis, and has been linked to "sick building" syndrome. Common indoor molds also include, for example, *penicillium, aspergillus, fusarium, cladosporium* and *alternaria*. Dry rot fungus in wood can be caused by a number of species, such as *Meruliporia incrassata, Serpula lacrymans* and *Serpula lacrymans*.

The term "subject" refers to an animal, typically a mammalian animal, such as primate (human, ape, gibbon, chimpanzee, orangutan, macaque), domestic animal (dog, cat, bird), farm animal (horse, cattle, goat, sheep, pig) and experimental animal (mouse, rat, rabbit, guinea pig). Subjects include animal disease models, e.g., a fungal disease animal model.

Subjects appropriate for treatment in accordance with the invention include those currently undergoing or candidates for anti-fungal treatment. Candidate subjects include, for example, subjects at risk of fungal contact, contamination or contracting a fungal infection. The invention methods are therefore applicable to treating a subject who is at risk of fungal contact, contamination, growth, proliferation or infection, but who has not yet exhibited overt symptoms. At risk subjects can be identified as having recurrent or frequent fungal infections, or that have increased risk of a fungal infection, such as an immune-suppressed subject (HIV), a subject undergoing or a candidate for immune-suppressive (organ or tissue transplant) or anti-cell proliferative (e.g., anti-cancer) therapy, or a subject exposed to an environment in which fungal contact, contamination, growth, proliferation or infection is or is likely to be present. At risk subjects include those using acrylic nails on one or more fingernails, which cause onychomycosis, a fungal infection of the nail plate. Subjects therefore include immuno-competent as well as immuno-compromised subjects.

The compounds of the invention, including peptides and peptidomimetics, can be combined with carriers, excipients and diluents suitable for pharmaceutical use. The invention therefore provides pharmaceutical compositions and formulations and methods of use, e.g., to treat fungal contact, contamination, growth, viability, proliferation or infection.

As used herein, a "pharmaceutical composition" or "pharmaceutical formulation" means a mixture of one or more invention compounds described herein, or a physiologically acceptable salt or prodrug thereof, with one or more additional chemical components, such as pharmaceutically acceptable or physiologically acceptable carriers and excipients. The terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. A "pharmaceutical composition" or "pharmaceutical formulation" therefore refers to a composition suitable for administration to a subject. A "pharmaceutically acceptable salt" means a compound in a charged form together with a counter-ion.

As used herein, "carrier" and "excipient" include solvents, dispersion media, vehicles, coatings, diluents, isotonic and absorption delaying agents, buffers, carrier solutions, suspensions, colloids, provide that they do not destroy activity or function of the active ingredient. An "excipient" further typically means an inert substance added to a pharmaceutical composition to further facilitate administration of a compound. Particular non-limiting examples of excipients include calcium carbonate, calcium phosphate, various sugars and types of starch, cellulose derivatives, gelatin, vegetable oils and polyethylene glycols.

Pharmaceutical compositions can be formulated to be compatible with a particular route of administration, systemic, regional or local. Thus, pharmaceutical compositions include carriers, diluents, or excipients suitable for administration by various routes.

Formulations or enteral (oral) administration can be contained in a tablet (coated or uncoated), capsule (hard or soft), microsphere, emulsion, powder, granule, crystal, suspension, syrup or elixir. Conventional nontoxic solid carriers which include, for example, pharmaceutical grades of mannitol, lactose, starch, magnesium stearate, sodium saccharin, talcum, cellulose, glucose, sucrose, magnesium carbonate, can be used to prepare solid formulations. Supplementary active compounds (e.g., preservatives, antibacterial, antiviral and antifungal agents) can also be incorporated into the formulations. A liquid formulation can also be used for enteral administration. The carrier can be selected from various oils including petroleum, animal, vegetable or synthetic, for example, peanut oil, soybean oil, mineral oil, sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Pharmaceutical compositions for enteral, parenteral, or transmucosal delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65–75; Warren (1997) J. Neurol. Sci. 152:31–38; and Tonegawa (1997) J. Exp. Med. 186:507–515. The parenteral preparation can be enclosed in ampules, disposable syringes or multiple dose vials made of glass or plastic.

Pharmaceutical compositions for intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride may be included in the composition. The resulting solutions can be packaged for use as is, or lyophilized, the lyophilized preparation can later be combined with a solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760–1764; Samanen (1996) J. Pharm. Pharmacol. 48:119–135; and U.S. Pat. No. 5,391,377).

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be through nasal sprays or suppositories (see, e.g., Sayani (1996) "Systemic delivery of peptides and proteins across absorptive mucosae" Crit. Rev. Ther. Drug Carrier Syst. 13:85–184). For transdermal administration, the compound can be formulated into ointments, salves, gels, foams, sprays, or creams known in the art. Any cream base for dermatological uses can be used. For a suppository, glycerin or paraffin can be used along with conventional thickening agents, such as hydroxypropylmethylcellulose to adjust viscosity. Transdermal delivery systems can also be achieved using patches.

For inhalation delivery, the pharmaceutical formulation can be administered in the form of an aerosol or mist. For aerosol administration, the formulation can be supplied in finely divided form along with a surfactant and propellant. In another embodiment, the device for delivering the formulation to respiratory tissue is in which the formulation vaporizes. Other delivery systems known in the art include dry powder aerosols, liquid delivery systems, inhalers, air jet nebulizers and propellant systems (see, e.g., Patton (1998) Biotechniques 16:141–143; Dura Pharmaceuticals, San Diego, Calif.; Aradigm, Hayward, Calif.; Aerogen, Santa Clara, Calif.; and Inhale Therapeutic Systems, San Carlos, Calif.).

Biodegradable, biocompatable polymers can be used, such as ethylene vinyl acetate, polyanhydrides, polyglycolic acid, collagen, polyorthoesters, and polylactic acid. Methods for preparation of such formulations are known in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known in the art, for example, as described in U.S. Pat. Nos. 4,235,871; 4,501,728; 4,522,811; 4,837,028; 6,110,490; 6,096,716; 5,283,185; 5,279,833; Akimaru (1995) Cytokines Mol. Ther. 1:197–210; Alving (1995) Immunol. Rev. 145:5–31; and Szoka (1980) Ann. Rev. Biophys. Bioeng. 9:467). Biodegradeable microspheres or capsules or other biodegradeable polymer configurations capable of sustained delivery of small molecules including peptides are known in the art (see, e.g., Putney (1998) Nat. Biotechnol. 16:153–157). Compounds of the invention can be incorporated within micelles (see, e.g., Suntres (1994) J. Pharm. Pharmacol. 46:23–28; Woodle (1992) Pharm. Res. 9:260–265). Peptides can be attached to the surface of the lipid monolayer or bilayer. For example, peptides can be attached to hydrazide-PEG-(distearoylphosphatidyl) ethanolamine-containing liposomes (see, e.g., Zalipsky (1995) Bioconjug. Chem. 6:705–708). Alternatively, any form of lipid membrane, such as a planar lipid membrane or the cell membrane of an intact cell, e.g., a red blood cell, can be used. Liposomal and lipid-containing formulations can be delivered by any means, including, for example, intravenous, transdermal (see, e.g., Vutla (1996) J. Pharm. Sci. 85:5–8), transmucosal, or oral administration.

A pharmaceutically acceptable formulation can incorporate about 0.11% to 99.9% of active ingredient (e.g., peptide or peptidomimetic). The pharmaceutical compositions can be sterilized by conventional, well-known sterilization techniques, or can be sterile filtered.

Additional pharmaceutical formulations and delivery systems are known in the art and are applicable in the methods and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms, Technonic Publishing Co., Inc., Lancaster, Pa., (1993); and Poznansky et al., Drug Delivery Systems, R. L. Juliano, ed., Oxford, N.Y. (1980), pp. 253–315)

The pharmaceutical formulations can be packaged in unit dosage form for ease of administration and uniformity of dosage. "Unit dosage form" as used herein refers to physically discrete unitary dosages for administration to the subject to be treated; each unit contains a predetermined quantity of compound in combination with a pharmaceutical carrier or excipient that produces a desired effect. "Multi-unit" dosage forms refer to multiple physically discret units each packaged for unitary administration according to a treatment protocol that produces a desired effect.

The invention compounds can also be used in combination with any treatment that has an anti-fungal activity or an anti-fungal function. Anti-fungal activity can thereby be increased, potentiated, synergized or prolonged by combining an invention compound with treatment that directly or indirectly inhibits fungal contact, contamination, growth, viability, proliferation or infection. Anti-fungal activity also can be increased, potentiated, synergized or prolonged by combining invention compounds with treatments that inhibit or suppress fungal contact, contamination, growth, viability, proliferation or infection, or reduce susceptibility to fungal contact, contamination, growth, proliferation or infection, whether or not such treatments damage nucleic acid. The invention therefore further provides compositions and methods of use including a compound of the invention (e.g., a peptide or peptidomimetic) and an anti-fungal treatment or agent, e.g., a nucleic acid damaging agent.

As used herein, the terms "anti-fungal treatment" and "anti-fungal agent" mean any treatment regimen or agent that directly or indirectly inhibits or reduces fungal growth, contamination or infection, or a symptom or condition associated with fungal growth, contamination or infection, or that decreases or reduces recurrence of or susceptibility to fungal growth, contamination or infection by a fungus, regardless of the mode of action, e.g., whether or not the treatment or agent damages nucleic acid. Particular examples of anti-fungal agents include drugs that inhibit cell proliferation. Specific examples include, inter alia, cyclophosphamide, azathioprine, cyclosporin A, prednisolone, melphalan, chlorambucil, mechlorethamine, busulphan, methotrexate, 6-mercaptopurine, thioguanine, cytosine arabinoside, taxol, vinblastine, vincristine, doxorubicin, actinomycin D, mithramycin, carmustine, lomustine, semustine, streptozotocin, hydroxyurea, cisplatin, mitotane, procarbazine, dacarbazine and dibromomannitol. Anti proliferative agents that cause nucleic acid replication errors or inhibit nucleic acid replication include nucleoside and nucleotide analogues, such as AZT and 5-AZC.

Suitable anti-fungal agents for animal (e.g., humans) or agricultural use, include allylamines (amrolfine, butenafine, naftifine, terbinafine), azoles (ketoconazole, fluconazole, elubiol, econazole, econaxole, itraconazole, isoconazole, imidazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, flutrimazole), polyenes (nystatin, pimaricin, amphotericin B), pyrimidines (flucytosine), tetraenes (natamycin), thiocarbamates (tolnaftate), sulfonamides (mafenide, dapsone), glucan synthesis inhibitors (caspofungin), benzoic acid compounds, complexes and derivatives thereof (actofunicone) and other systemic or mucosal (griseofulvin, potassium iodide, Gentian Violet) and topical drugs (ciclopirox, ciclopirox olamine, haloprogin, undecylenate, silver sulfadiazine, undecylenic acid, undecylenic alkanolamide, Carbol-Fuchsin). Other suitable anti-fungal agents for use in animals are decribed, for example, in *Physicians Desk Reference*, 57$^{th}$ ed., November 2002, Medical Economics Company.

Suitable anti-fungal agents for agricultural or horticultural use include mancozeb, manzate, Banner Maxx, Compass Cleary's, Funginex, Immunox, Dithane, Eagle, Fore, Systhane, Topsin, captan, thiram, carboxin, mefenoxan, PCNB, fludioxonil, thiabendazole, copper-based fungicides (e.g., copper oxychloride), sulfur compounds, citrus oils and *Bacillus subtilis*. Other suitable anti-fungal agents for agricultural use are decribed, for example, in *Fungicides in Plant Disease Control*, 3$^{rd}$ ed., Nen and Thapliyal, 1993, Science Publishers Inc.

Suitable anti-fungal agents for industrial, residential, community and commercial use include, for example, detergents, bleach, OMACIDE® IPBC (3-iodopropynylbutycarbamate), Fungitrol®, Nuocept®, microban, citrus oils and chromated copper arsenate (wood preservative).

As used herein, the terms "nucleic acid damaging treatment" and "nucleic acid damaging agent" means any treatment regimen that directly or indirectly damages nucleic acid (e.g., DNA, cDNA, genomic DNA, mRNA, tRNA or rRNA). Specific examples of such agents include alkylating agents, nitrosoureas, anti-metabolites, plant alkaloids, plant extracts and radioisotopes. Specific examples of agents also include nucleic acid damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochloride (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubibcin (Cerubicine), idarubicin (Idamycin) and epirubicin (Ellence), anthracyclin analogues such as mitoxantrone, actinimycin D, non intercalating topoisomerase inhibitors such as epipodophyllotoxins (etoposide=VP16, teniposide=VM-26), podophylotoxin, bleomycin (Bleo), pepleomycin, compounds that form adducts with nucleic acid including platinum derivatives (e.g., cisplatin (CDDP), trans analogue of cisplatin, carboplatin, iproplatin, tetraplatin and oxaliplatin), camptothecin, topotecan, irinotecan (CPT-11), and SN-38. Specific examples of nucleic acid damaging treatments include radiation (e.g., ultraviolet (UV), infrared (IR), or alpha-, beta- or gamma-radiation) and environmental shock (e.g., hyperthermia).

Invention methods and compositions including peptides and peptidomimetics can be combined with other agents or treatments that may provide benefit. For example, fungal contact, contamination, growth, proliferation or infection are often associated with other pathogens, such as bacteria, viruses and parasites. In particular, subjects at risk of opportunistic fungal infection, such as immuno-compromised patients (e.g., due to organ or tissue transplant or HIV infection) are also at risk of viral, bacterial, parasitic and other infections. Thus, an anti-mcrobial agent or treatment (anti-viral or anti-bacterial or anti-parasitic agent) can be combined with an invention peptide or peptidomimetic. The invention therefore provides methods and compositions including combinations with bacterial, viral and parasitic treatments and agents.

In addition, fungal contact, contamination, growth, proliferation or infection may produce inflammation. Thus, an anti-inflammatory agent or treatment can be combined with an invention peptide or peptidomimetic composition or method. Fungal contact, contamination, growth, proliferation or infection may also produce pain or swelling. Thus, an analgesic or pain-relieving agent or treatment can be combined with an invention peptide or peptidomimetic.

Anti-inflammatory agents or treatments include, for example, steroidal and non-steroidal based drugs and therapies. Steroidal anti-inflammatory agents include glucocorticoids. Non-limiting examples of steroids include fluocinolone, triamcinolone, triamcinoline acetonide, betamethasone, betamethasone diproprionate, diflucortolone, fluticasone, cortisone, hydrocortisone, mometasone, methylprednisolone, beclomethasone diproprionate, clobetasol, prednisone, prednisolone, meythylprednisolone, betamethasone, budesonide, dexamethasone, and. Non-limiting examples of non-steroidal anti-inflammatory agents include celocoxib, nimesulide, rofecoxib, meclofenamic acid, meclofenamate sodium, flunixin, fluprofen, flurbiprofen, sulindac, meloxicam, piroxicam, etodolac, fenoprofen, fenbuprofen, ketoprofen, suprofen, diclofenac, bromfenac sodium, phenylbutazone, thalidomide and indomethacin.

Analgesics and pain-relieving agents and treatments, some of which possess anti-inflammatory activity, include aspirin, acetaminophen, ibuprofin, naproxen, procaine, lidocaine, tetracaine, dibucaine, benzocaine, p-buthylaminobenzoic acid 2-(diethylamino) ethyl ester HCl, mepivacaine, piperocaine, and dyclonine. Other analgesics include opioids such as, for example, morphine, codeine, hydrocodone and oxycodone.

Antiviral agents or treatments inhibit, reduce or eliminate virus replication, proliferation or a symptom or condition associated with or caused by virus replication or proliferation. Antiviral agents and treatments therefore include any agent or treatment capable of inhibiting, reducing, preventing or modulating viral infection or production at any step or stage of the viral life cycle, for example, virus fusion to a cell via a cell surface receptor or independent of a cell surface receptor; entry of viral nucleic acid into the cell; reverse transcription of viral nucleic acid; integration of reverse transcribed viral nucleic acid into the genome of the cell; proviral nucleic acid transcription or replication; translation or formation of mature viral proteins; formation/assembly of infectious viral particles; budding or release of mature virions from a cell.

Particular non-limiting examples of antiviral agents include viral fusion inhibitors, e.g., T20 and T20 analogues (Trimeris, Inc.); non-nucleoside reverse transcriptase inhibitors (e.g., nevirapine, delavirdine, efavirenz); protease inhibitors (e.g., saquinavir, ritonavir, indinavir, nelfinavir, amprenavir); thymidine kinase inhibitors; sugar or glycoprotein synthesis inhibitors; structural protein synthesis inhibitors; nucleoside analogues (e.g., zidovudine (AZT), stavudine (d4T), larnivudine (3TC), didanosine (DDI), zalcitabine (ddC), abacavir, acyclovir, penciclovir, valacyclovir and ganciclovir); and viral maturation inhibitors (e.g., "zinc finger injectors," which inhibit proper viral a nuclear capsid protein assembly thereby preventing formation of infectious viral particles).

Industrial, residential, community, commercial, agricultural, horticultural and environmental settings appropriate for treatment in accordance with the invention can be identified by detecting the presence of a fungus in the particular setting. For example, to determine if a fungus exists in a structure, sampling can be done both indoors and outdoors. If the amount of fungus indoors exceeds what is outside, then it is likely that fungal contamination exists. For example, air within a building or other structure can be examined for molds. A general estimate of the number and different types of mold particles (spores and conidia) can be made by microscopic examination of particles impacted upon a filter or microscope slide. Alternatively, any fungi in the air may be impacted upon a growth medium. Growth in the laboratory allows an accurate identification of the viable fungi that were in the air where the sample was taken. Visual inspection can also reveal the presence of fungus. For example, one can observe for molds growing on or within a building or other structure. The content of vacuum cleaner bags can be examined, or specimens can be swabbed from surfaces, or cut out and pieces of material that appear to have fungal growth identified.

Invention compounds can be administered prior to, contemporaneously with or following other treatment protocols or agents, prior to, contemporaneously with or following fungal infection, contamination or growth. Thus, combination prophylactic treatment methods as well as methods where it is desired to reduce or inhibit recurrence of fungal contact, contamination, growth, proliferation or infection are provided.

The invention therefore additionally provides combination methods and treatments for inhibiting, decreasing and reducing fungal contact, contamination, growth, viability, proliferation and infection in vitro, ex vivo and in vivo. Treatments for use in combination with invention compounds include any anti-fungal, nucleic acid damaging or anti-tumor treatment or agent disclosed herein or known in the art. For example, a chemotherapeutic treatment may comprise radiation treatment via an external source of radiation or internalization of a radioisotope, optionally in combination with drug treatment. The treatment may therefore include administration of a chemical substance, such as a radioisotope, or a drug, such as a chemotherapeutic agent.

Amounts administered for treatment are typically in an "effective amount" or "sufficient amount" that is, an amount sufficient to produce a desired affect. Effective amounts therefore include one or more of: inhibiting or reducing susceptibility to or recurrence of fungal contact, contamination, growth, proliferation or infection; reducing, decreasing or inhibiting fungal contamination, growth, viability, proliferation or infection (e.g., reduces or eliminates the fungal cells); and reducing or decreasing one or more symptoms associated with or caused by fungal c contact, contamination, growth, viability, proliferation or infection, relative to an appropriate control. The amount can therefore be sufficient to reduce the infection, or stabilize the infection (e.g., inhibit or prevent the progression or worsening of a fungal contamination, growth, proliferation or infection, or one or more symptoms associated with or caused by fungal contact, contamination, growth, proliferation or infection). Thus, amounts considered effective can prevent or inhibit progression of the infection or an associated condition or disorder.

Effective amounts can objectively or subjectively reduce or decrease the severity, frequency or duration of one or more symptoms associated with or caused by fungal contact, contamination, growth, viability, proliferation or infection, or an associated disorder or condition. For example, an amount of an invention compound that reduces severity, frequency or duration of itching, inflammation, pain, discharge or any other symptom or associated condition is a satisfactory clinical endpoint. Effective amounts can also result in a histological improvement.

Effective amounts also include a reduction of the amount (e.g., dosage) or frequency of treatment with another anti-fungal treatment, which is considered a satisfactory clinical endpoint. For example, a subject treated with an invention compound may require less nucleic acid damaging treatment in order to treat the fungal infection. An effective amount would include an amount that reduces the dosage frequency or amount of an anti-fungal treatment administered in combination in comparison to the dosage frequency or amount administered without treatment with a compound of the invention.

A "therapeutically effective amount" means an amount that reduces or ameliorates one or more of the symptoms associated with or caused by fungal contact, contamination, growth, viability, proliferation or infection, i.e., an "improvement" of the subject's condition or "therapeutic benefit" to the subject.

A "prophylactically effective amount" means an amount that decreases or reduces susceptibility to fungal contamination, growth, proliferation or infection; or that maintains inhibition of growth or proliferation of fungal cells achieved by administration of an anti-fungal treatment or agent; or that maintains inhibition of the spread or worsening of a fungal infection achieved by administration of an anti-fungal treatment or agent; or that maintains a reduction in one or more symptoms caused by or associated with fungal contamination, growth, proliferation or infection. A prophylactically effective amount also means an amount that will inhibit or prevent a fungus from contacting, contaminating, growing, proliferating or infecting a susceptible object (e.g., a living organism). The term "ameliorate," when referring to a subject having or at risk of having fungal contact, contamination, growth, proliferation or infection, is used synonymously.

Exemplary amounts for CBP501 are approximately 1 to 20 uM in vitro, or about 2 to 40 ug/ml. Systemic exemplary amounts for CBP501 are approximately 1 to 10 mg/kg, or about 3 to 30 mg/mm (iv); or approximately 5 to 50 mg/kg, or about 15 to 150 mg/mm (ip). Amounts in mm are about equal in most of animals, thus in humans, for example, amounts would be about 3 to 30 mg/mm by infusion. For the topical use, approximately 20 microgram for 1 square cm of skin should be sufficient.

Methods of the invention that lead to an improvement in the subject's condition or a therapeutic benefit may be relatively short in duration, e.g., the improvement may last several minutes, hours, days or weeks, or extend over a longer period of time, e.g., months or years. An effective amount therefore need not be a complete ablation or elimination of fungal contact, contamination, growth, viability, proliferation or infection, or any or all symptoms associated with or caused by fungal contact, contamination, growth, viability, proliferation or infection. Thus, a satisfactory clinical endpoint for an effective amount is achieved when there is a subjective or objective improvement in the subjects' condition, as determined using any of the foregoing criteria or other criteria known in the art appropriate for determining the status or degree of fungal contact, contamination, growth, viability, proliferation or infection, or susceptibility or recurrence of fungal contact, contamination, growth, proliferation or infection, over a short or long period of time.

An effective amount of an invention compound for treating a subject can be determined in vitro based upon comparison to an amount of an anti-fungal agent that is known to have activity in animals at a given concentration or dosage. For example, susceptibility testing can be used to determine a minimal concentration of compound that inhibits or reduces fungus growth or proliferation; inhibits or reduces the amount of fungus (minimum inhibitory concentration, MIC, µg/ml) or kills the fungus (minimum fungicidal concentration, MFC, µg/ml). Alternatively, animal studies including human clinical trials can be used to determine effective amounts.

The skilled artisan will appreciate the various factors that may influence the dosage and timing required to treat a particular subject including, for example, the general health, age, or gender of the subject, the severity or stage of the disorder or condition, previous treatments, susceptibility to undesirable side effects, clinical outcome desired and the presence of other disorders or conditions. Such factors may influence the dosage and timing required to provide an amount sufficient for therapeutic benefit.

In the methods of the invention for treating a subject, compounds of the invention can be administered systemically, regionally (e.g., directed towards an organ or tissue), or locally (e.g., intracavity or topically onto the skin), in accordance with any protocol or route that achieves a desired effect. The compounds can be administered as a single or multiple dose each day (e.g., at a low dose), intermittently (e.g., every other day, once a week, etc. at a higher dose), or continuously, as determined by the treating medical professional. The compounds as well as pharmaceutical compositions including one or more of the compositions alone, or in a combiantion, can be administered via inhalation (e.g., intra-tracheal), orally, intravenously, intraarterially, intravascularly, intrathecally, intraperitonealy, intramuscularly, subcutaneously, intracavity, transdermally (e.g., topical), transmucosally (e.g., buccal, vaginal, uterine, rectal, or nasal), by multiple administrations, sustained release (e.g., continuos infusion, gradual perfusion over time or capsules) or a single bolus.

Compounds administered topically are typically applied in unit doses ranging from 1 mg/mL to 1 gm/mL, or in doses ranging from 1 mg/mL to 100 mg/mL. Compounds administered intravenously (IV) typically would be from about 0.01 mg/hr to about 1.0 mg/hr over several hours (typically 1, 3, or 6 hours), which can be repeated for one or more weeks with intermittent cycles. One or more daily doses typically range from 0.1 mg/kg to 100 mg/kg per day, from 0.1 mg/kg to 20 mg/kg per day, or from 1 to 20 mg/kg/day. Considerably higher dosages (e.g., ranging up to about 10 mg/ml) can be used, particularly when the drug is administered locally or regionally, and not into the blood stream, such as into a body cavity or into a lumen of an organ, e.g., vagina. One skilled in the art can readily ascertain effective dosages and administration protocols to achieve a therapeutic benefit.

The compounds may be delivered using a sustained-release system, such as semipermeable matrices of solid hydrophobic polymers. Sustained-release systems and methods, including microfabricated devices for sustained internal delivery, are known the in the art.

The invention further provides kits including invention compounds and pharmaceutical formulations thereof, optionally packaged into suitable packaging material. A kit typically includes a label or packaging insert including a description of the components or instructions for use in vitro, in vivo, or ex vivo, in the environment, in an agricultural or horticultural setting, or in a commercial, industrial, residential or community setting of the components therein. The label optionally includes a listing of the particular genus or species of fungus appropriate for treatment. A kit can contain a collection of such components, e.g., two or more invention compounds or an invention compound in combination with an anti-fungal agent.

The term "packaging material" means to a physical structure housing the components of the kit. The packaging material can maintain the components sterilely, and can be made of material commonly used for such purposes (e.g., paper, corrugated fiber, glass, plastic, metal, foil, ampules, etc.). The label or packaging insert can include appropriate written instructions. Kits of the invention therefore can additionally include labels or instructions for using the kit components in any method of the invention. Instructions can include instructions for practicing any of the methods of the invention described herein. Thus, for example, a kit can include an invention compound in a pack, or dispenser together with instructions for administering the compound in a treatment method of the invention. Instructions may additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

Invention kits can additionally include a buffering agent, a preservative or a stabilizing agent, in a pharmaceutical formulation. Each component of the kit can be enclosed within an individual container and all of the various containers can be within a single package. Invention kits can be designed for cold storage.

The invention additionally provides articles of manufacture that include invention compounds and pharmaceutical formulations thereof. The term "object" as defined herein is intended to include articles of manufacture.

Articles of manufacture include machinery, equipment, instruments, devices, packaging material, or any organic or inorganic material (e.g., a construction material or a medical material) that may come into contact with a fungus.

As used herein, the term "medical material," refers to any object used in a health care setting to which a patient or subject may be exposed during the course of examination, diagnosis or treatment. Particular non-limiting examples of medical materials include sutures, wound dressings (occlusive and semi-occlusive fabrics, e.g., gauze pads or bandages), topical patches, adhesive films, casts, tapes and fasteners. Additional non-limiting examples of medical materials include examination gloves, gowns and masks, syringes and needles.

The invention moreover provides use of the peptides and peptidomimetics of the invention, e.g., a sequence having 90% or more identity to a sequence set forth herein, or a prodrug thereof, for the manufacture of a medicament sufficient to inhibit, reduce or prevent fungal contact, contamination, growth, proliferation or infection. The medicament optionally includes other agents, such as an anti-microbial, anti-inflammatory or analgesic agent, or a pharmaceutically acceptable or physiologically acceptable carrier or excipient.

Methods of identifying and screening for compounds having an anti-fungal activity or function are provided. The methods of identifying and screening can be performed in solution or in solid phase, in vitro (cell or tissue culture), ex vivo, or in vivo (in an animal).

In one embodiment, a method includes contacting a compund that abrogates or inhibits G2 checkpoint with a fungus; incubating the fungus with the compound; and determining viability, growth or proliferation of the fungus. Reduced viability, growth or proliferation of the fungus in the presence of the compound identifies the compound as having anti-fungal activity. In another embodiment, a method includes contacting a compund that abrogates or inhibits G2 checkpoint with a fungus; incubating the fungus with the compound; and determining viability, growth or proliferation of the fungus. In a further embodiment, a method includes contacting a peptide or peptidomimetic with a fungus; incubating the fungus with the peptide or peptidomimetic; and determining viability, growth or proliferation of the fungus. Reduced viability, growth or proliferation of the fungus in the presence of the peptide or peptidomimetic identifies the peptide or peptidomimetic as having anti-fungal activity. In yet another embodiment, a method includes contacting a peptide or peptidomimetic with a fungus; incubating the fungus with the peptide or peptidomimetic; and determining viability, growth or proliferation of the fungus.

The following are abbreviations used herein:
Cha: cyclohexyl-alanine
Phe-2,3,4,5,6-F: Fluorides are at position 2,3,4,5,6, on Phenyl residue of Phenylalanine
F: Fluoride
Bpa: Benzoyl-phenylalanine
Nal(2): 2-Naphthyl-alanyl
Ala(3-Bzt): (3-Benzothienyl)-Alanine
Nal(1): 1-Naphthyl-alanyl
Dph: Diphenyl-Alanine
Ala(tBu): t-Butyl-alanyl
Cys(tBu): t-Butyl-cysteine
Phe-3,4,5-F: Fluorides are at position 3,4,5 on the Phenyl of Phenylalanine
Phe-4CF3: CF3 is at position 4 on Phenyl residue of Phenylalanine
Phe-3Br,4Cl,5Br: Bromide is at position 3, Chloride is at position 4, and Bromide is at position 5 on the Phenyl of Phenylalanine
Phe-4Cl: Chloride is at position 4 on the Phenyl of Phenylalanine P1, P2, P3, P4, P5, P6, etc., and (P1, P2, P3, P4, P5, P6, etc.); and P7, P8, P9, P10, P11, P12, etc., and (P7, P8, P9, P10, P11, P12, etc.); and $X_1$, $X_2$, $X_3$, X4, $X_5$, $X_6$, $X_7$, $X_8$, $X_9$, $X_{10}$, $X_{11}$: contiguous sequence of P1, P2, P3, P4, P5, P6, etc.; and P7, P8, P9, P10, P11, P12, and $X_1$, $X_2$, $X_3$, $X_4$, $X_5$, $X_6$, $X_7$, $X_8$, $X_9$, $X_{10}$, $X_{11}$, respectively.

X: Any amino acid

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," "the" and "is" include plural referents unless the context clearly indicates otherwise. Thus, for example, reference to a "compound" includes a plurality of compounds and reference to "a peptide" or an "amino acid" includes reference to one or more peptides and amino acids, as appropriate.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes materials and several methods.

Chemicals and reagents Amphotericin B was purchased from Sigma-Aldrich Co. (St. Louis, Mo.) and it was dissolved in DMSO to 10 mg/ml. Boromycin and L,L-D42067α were kindly provided from Prof. H. Tomoda at Kitasato University.

Cell culture Saccaromices Cerevisie AH109 was purchased from CLONTECH (Palo Alto, Calif.). YAPD plates were prepared using YPD agar purchased from CLONTECH and adenine purchased from Sigma-Aldrich Co. The cells were cultured at 30 degree.

Example 2

This example describes structure of various compounds of the invention. Table 1 illutrates various peptides/peptidomimetics, including CBP501 ((d-Bpa)(d-Ser)(d-Trp)(d-Ser)(d-Phe2,3,4,5,6-F)(d-Cha)(d-Arg)(d-Arg)(d-Arg)(d-Gln)(d-Arg)(d-Arg)).

TABLE 1

Sequences and Corresponding Code Names
of exemplary peptides/peptidomimetics.

| | |
|---|---|
| (l-Tyr)(l-Gly)(l-Arg)(l-Lys)(l-Lys)(l-Arg)(l-Arg)(l-Lys) | (SEQ ID NO: 116) CBP413 |
| (l-Arg)(l-Arg)(l-Arg)(l-Cha)(l-Phe-2,3,4,5,6-F) | |
| (l-Arg)(l-Ser)(l-Pro)(l-Ser)(l-Tyr)(l-Tyr) | |

TABLE 1-continued

Sequences and Corresponding Code Names
of exemplary peptides/peptidomimetics.

| Sequence | SEQ ID NO | Code |
|---|---|---|
| (l-Tyr)(l-Gly)(l-Arg)(l-Lys)(l-Lys)(l-Arg)(l-Gln)(l-Arg)(l-Arg)(l-Arg)(l-Cha)(l-Phe-2,3,4,5,6-F)(l-Arg)(l-Ser)(l-Pro)(l-Ser)(l-Tyr) | SEQ ID NO: 117 | CBP420 |
| (l-Arg)(l-Arg)(l-Arg)(l-Cha)(l-Phe-2,3,4,5,6-F)(l-Arg)(l-Ser)(l-Pro)(l-Ser)(l-Tyr)(l-Tyr) | SEQ ID NO: 118 | CBP430 |
| (l-Arg)(l-Arg)(l-Gln)(l-Arg)(l-Arg)(l-Arg)(l-Cha)(l-Phe-2,3,4,5,6-F)(l-Arg)(l-Ser)(l-Pro)(l-Ser)(l-Tyr)(l-Tyr) | SEQ ID NO: 119 | CBP431 |
| (l-Arg)(l-Arg)(l-Gln)(l-Arg)(l-Arg)(l-Arg)(l-Cha)(l-Phe-2,3,4,5,6-F)(d-Ser)(d-Trp)(l-Pro)(l-Ser)(l-Tyr) | | CBP432 |
| (l-Tyr)(l-Gly)(l-Arg)(l-Lys)(l-Lys)(l-Arg)(l-Arg)(l-Gln)(l-Arg)(l-Arg)(l-Arg)(l-Cha)(l-Phe-2,3,4,5,6-F)(l-aminoundecanoic acid)(l-Tyr)(l-Tyr) | SEQ ID NO: 120 | CBP440 |
| (d-Tyr)(d-Tyr)(d-Ser)(l-Gly)(d-Ser)(d-Arg)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) | | CBP450 |
| (d-Tyr)(d-Ser)(d-Pro)(l-Trp)(l-Ser)(d-Phe-2,3,4,5,6-F)(d-Cha)(d-Arg)(d-Arg)(d-Arg)(d-Gln)(d-Arg)(d-Arg) | | CBP451 |
| (d-Tyr)(d-Ser)(l-Pro)(l-Trp)(l-Ser)(d-Phe-2,3,4,5,6-F)(d-Cha)(d-Arg)(d-Arg)(d-Arg)(d-Gln)(d-Arg)(d-Arg) | | CBP452 |
| (d-Tyr)(d-Ser)(d-Pro)(l-Trp)(l-Ser)(d-Phe-2,3,4,5,6-F)(d-Pro)(d-Arg)(d-Arg)(d-Arg)(d-Gln)(d-Arg)(d-Arg) | | CBP454 |
| (d-Tyr)(d-Ser)(d-Pro)(l-Trp)(l-Ser)(d-Phe-2,3,4,5,6-F)(l-Pro)(d-Arg)(d-Arg)(d-Arg)(d-Gln)(d-Arg)(d-Arg) | | CBP455 |
| (l-Tyr)(l-Tyr)(l-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) | | CBP460 |
| (l-Tyr)(l-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) | | CBP461 |
| (l-Tyr)(l-aminoundecanoic acid)(d-Phe-2,3,4,5,6-F)(d-Cha) | | CBP462 |
| (l-aminoundecanoic acid)(d-Phe-2,3,4,5,6-F)(d-Cha)(d-Arg) (d-Arg) (d-Arg) (d-Gln) (d-Arg) (d-Arg)(d-Lys)(d-Lys)(d-Arg)(l-Gly)(d-Tyr) | | CBP463 |
| (l-aminoundecanoic acid)(d-Phe-2,3,4,5,6-F)(d-Cha) | | CBP464 |

TABLE 1-continued

Sequences and Corresponding Code Names of exemplary peptides/peptidomimetics.

| Sequence | Code |
|---|---|
| (l-aminoundecanoic acid)(d-Phe-2,3,4,5,6-F)(d-Cha) (d-Arg)(d-Arg)(d-Arg) (d-Gln) (d-Arg) (d-Arg) | CBP465 |
| (l-8-aminocaprylic acid)(d-Cha)(d-Phe-2,3,4,5,6-F) (d-Arg)(d-Arg)(d-Arg)(d-Gln) (d-Arg) (d-Arg) | CBP466 |
| (d-Phe-2,3,4,5,6-F)(d-Cha) | CBP470 |
| (d-Cha)(d-Phe-2,3,4,5,6-F) (d-Arg)(d-Arg)(d-Arg) (d-Gln)(d-Arg)(d-Arg) | CBP471 |
| (d-Tyr)(d-Ser)(d-Ser)(d-Trp)(d-Ser)(d-Phe-2,3,4, 5,6-F)(d-Cha) (d-Arg)(d-Arg)(d-Arg) (d-Gln) (d-Arg)(d-Arg) | CBP481 |
| (d-Tyr)(d-Bpa)(d-Ser)(d-Trp)(d-Ser)(d-Phe-2,3,4, 5,6-F)(d-Cha) (d-Arg)(d-Arg)(d-Arg)(d-Gln) (d-Arg) (d-Arg) | CBP500 |
| (d-Bpa) (d-Ser)(d-Trp)(d-Ser) (d-Phe-2,3,4,5,6-F) (d-Cha) (d-Arg) (d-Arg) (d-Arg) (d-Gln) (d-Arg) (d-Arg) | CBP501 |
| (d-Bpa)(l-8-aminocaprylic acid)(d-Cha) (d-Phe-2,3,4,5,6-F) (d-Arg) (d-Arg) (d-Arg) (d-Gln) (d-Arg) (d-Arg) | CBP502 |
| (d-Bpa)(l-8-aminocaprylic acid)(d-Phe-2,3,4,5,6-F) (d-Cha) (d-Arg) (d-Arg) (d-Arg) (d-Gln) (d-Arg) (d-Arg) | CBP503 |
| (d-Asp) (d-Bpa) (d-Ser) (d-Trp) (d-Ser) (d-Phe-2,3,4,5,6-F) (d-Cha) (d-Arg) (d-Arg) (d-Arg) (d-Gln) (d-Arg) (d-Arg) | CBP504 |
| (d-Bpa) (d-Asp) (d-Ser) (d-Trp) (d-Ser) (d-Phe-2,3,4,5,6-F) (d-Cha) (d-Arg) (d-Arg) (d-Arg) (d-Gln) (d-Arg) (d-Arg) | CBP505 |
| (d-Bpa) (d-Ser) (d-Trp) (d-Ser) (d-Asp) (d-Phe-2,3,4, 5,6-F)(d-Cha) (d-Arg) (d-Arg) (d-Arg) (d-Gln) (d-Arg) (d-Arg) | CBP506 |
| (d-Arg) (d-Arg) (d-Arg) (d-Gln) (d-Arg) (d-Arg) (d-Cha) (d-Phe-2,3,4,5,6-F) (d-Ser) (d-Trp) (d-Ser) (d-Bpa) | CBP510 |
| (d-Arg) (d-Arg) (d-Arg) (d-Gln) (d-Arg) (d-Arg) (d-Bpa) (d-Ser) (d-Trp) (d-Ser) (d-Phe-2,3,4,5.6-F) (d-Cha) | CBP511 |

TABLE 1-continued

Sequences and Corresponding Code Names of exemplary peptides/peptidomimetics.

| Sequence | Code |
|---|---|
| (d-Arg) (d-Arg) (d-Arg) (d-Arg) (d-Arg) (d-Arg) (d-Cha) (d-Phe-2,3,4,5,6-F) (d-Ser) (d-Trp) (d-Ser) (d-Bpa) | CBP512 |
| (d-Bpa)(d-Ser)(d-Trp)(d-Ser)(d-Bpa)(d-Cha)(d-Arg) (d-Arg) (d-Arg) (d-Gln) (d-Arg) (d-Arg) | CBP601 |
| (d-Bpa)(1-8-aminocaprylic acid) (d-Bpa) (d-Cha) (d-Arg) (d-Arg) (d-Arg) (d-Gln) (d-Arg) (d-Arg) | CBP602 |
| (d-Bpa)(d-Ser)(d-Trp)(d-Ser)(d-Phe4No2)(d-Cha)(d-Arg) (d-Arg) (d-Arg) (d-Gln) (d-Arg) (d-Arg) | CBP603 |
| (d-Bpa)(d-Pro)(d-Trp)(d-Pro)(d-Phe4NO2)(d-Cha)(d-Arg) (d-Arg) (d-Arg) (d-Gln) (d-Arg) (d-Arg) | CBP604 |
| (d-Bpa)(d-Pro)(d-Trp)(d-Pro)(d-Phe4NO2)(d-Nal2)(d-Arg) (d-Arg) (d-Arg) (d-Gln) (d-Arg) (d-Arg) | CBP605 |
| (d-Phe4NO2)(d-Pro)(d-Trp)(d-Pro)(d-Phe4NO2)(d-Cha) (d-Arg) (d-Arg) (d-Arg) (d-Gln) (d-Arg) (d-Arg) | CBP606 |
| (d-Bpa) (d-Ser) (d-Trp) (d-Ser) (d-Phe-2,3,4,5,6-F) (d-Cha)(d-Arg) (d-Arg) (d-Arg) (d-Arg) (d-Arg) | CBP607 |
| (d-Bpa) (d-Ser) (d-Trp) (d-Ser) (d-Phe-2,3,4,5,6-F) (d-Cha)(d-Arg) (d-Arg) (d-Arg) (d-Arg) (d-Arg) (d-Arg) | CBP608 |
| (d-Bpa)(d-Ser)(d-Trp)(d-Ser) (d-Phe-2,3,4,5,6-F) (d-Cha) (d-Lys)(d-Lys)(d-Lys)(d-Lys) (d-Lys) (d-Lys) | CBP609 |
| (d-Arg) (d-Arg) (d-Bpa)(d-Arg) (d-Arg) (d-Arg) (d-Phe-2,3,4,5,6-F)(d-Cha) | CBP700 |
| (d-Arg) (d-Arg) (d-Arg) (d-Bpa)(d-Arg)(d-Trp)(d-Arg) (d-Phe-2,3,4,5,6-F)(d-Cha) | CBP701 |
| (d-Arg) (d-Arg) (d-Arg) (d-Arg) (d-Bpa)(d-Arg)(d-Trp) (d-Arg)(d-Phe-2,3,4,5,6-F)(d-Cha) | CBP702 |
| (d-Arg) (d-Arg) (d-Arg)(d-Bpa)(d-Arg) (d-Arg) (d-Arg) (d-Phe-2,3,4,5,6-F)(d-Cha) | CBP703 |
| (d-Bpa)(d-Cys)(d-Trp)(d-Arg)(d-Phe-2,3,4,5,6F)(d-Cha) (d-Cys) | CBP524 |
| (d-Tyr)(d-Cys)(d-Pro)(d-Trp)(d-Arg)(d-Phe-2,3,4,5,6F) (d-Cha)(d-Cys) | CBP721 |

Example 3

This example indicates the phosphorylation inhibition activity of CBP501. As shown in FIG. 1, CBP501 strongly inhibited the activity of kinases involved in the cell cycle G2 checkpoint, such as ATM, ATR, CHK1, CHK2, PLK1, and Wee1, as compared to other serine-threonine kinases such as cyclin-dependent kinases, PKA and PKC.

Source of kinases, measurement method, substrate, first antibody, second antibody, reaction buffer, reaction volume, ATP concentration, and reaction time are as follows. ATM and ATR: Full length recombinant human, 293T cells, enzyme linked immunosorbent assay (ELISA), GST-p53 (aa1 -99), anti-p53-phosphorylated Ser1 5, Horse radish peroxidase (HRP)-labeled anti-rabbit IgG, 1×Mg/Mn kinase buffer (20 mM Hepes-KOH (pH7.5), 1 mM DTT, 80 ug/ml BSA, 10 mM MgCl2, 10 mM MnCl$_2$), 50 ul, 100 uM, and 60 min. Chk1, Chk2 and c-Tak1: Full length recombinant human from SF-9 cells for Chk1, Full length recombinant human from E. Coli for Chk2 and Full length recombinant human from SF-9 cells for c-Tak1, respectively, ELISA, GST-Cdc25C (aa167–267), anti-Cdc25C-phosphorylated Ser216, HRP-labelled anti-mouse IgG, 1×Mg kinase buffer (20 mM Hepes-KOH (pH7.5), 1 mM DTT, 80 ug/ml BSA, 10 mM MgCl$_2$), 50 ul, 50 uM, and 60 min. PLK-1: Human full length GST fusion, E. Coli, ELISA, GST fusion protein Y, Anti-phosphorylated Ser/Thr monoclonal, HRP-labelled anti-mousr IgG, 1×Mg kinase buffer, 30 ul, 50 uM, and 60 min. Wee1: Human fulllength recombinant with GST fusion, E. Coli, ELISA, Anti-Cdc2-phosphorylated Tyr15, HRP-labeled anti-rabbit IgG, 1×Mg kinase buffer, 50 ul, 100 uM, and 60 min. DNA-PK: Human purifed, HeLa cells, ELISA, GST-p53 (aa1–99), anti-p53-phosphorylated Ser15, HRP-labeled anti-rabbit IgG, 1×Mg kinase buffer, 50 ul, 100 uM, and 60 min. Cdk2-Cyclin A, Cdc2-Cyclin B, Cdk2-Cyclin E, and Cdk4-CyclinD1: Full length human recombinant, SF-9 cells, sandwich ELISA, Anti-RB-phosphorylated Thr356, Ser612, Thr356 and Thr356, respectively, HRP-labeled anti-RB mouse monoclonal, 1×Cdk/Cyclin reaction buffer (50 mM Hepes-KOH (pH7.5), 1 mM EGTA, 1 mM DTT, 200 ug/ml BSA, 15 mM MgCl$_2$, 0.02% Tween-20, 10% Glycerol), 50 ul, 100 uM, and 30 min. Cdk5-p25: Human full length recombinant with GST fusion, E. Coli, Glass filter trapping assay using gamma-32ATP, Histone H1, 1×Mg kinase buffer, 30 ul, 25 uM, and 60 min. PKA: Human recombinant catalytic subunit, E. Coli, ELISA, PS peptide, Biotinylated mouse monoclonal antibody 2B9, HRP streptavidin, 1×PKA reaction buffer (20 mM Tris HCl (pH7.0), 3 mM MgCl$_2$), 50 ul, 100 uM, and 30 min. PKC: purified rat, rat brain, ELISA, PS peptide, Biotinylated mouse monoclonal antibody 2B9, HRP conjugated streptavidin, 1×PKC buffer (20 mM Tris HCl (pH7.0), 3 mM MgCl$_2$, 2 mM CaCl$_2$, 50 ug/ml phosphatidylserine), 50 ul, 100 uM, and 30 min.

All incubations were at 30° C. Phosphorylation inhibition analysis was performed as follows. Each kinase, ATP and substrate were incubated with or without CBP501 (0.5, 5, 50 uM) at 30° C. in the above indicated buffer for the indicated time. The phosphorylated substrate was detected with either ELISA or RIA as described above. The percent phosphorylation of substrate was plotted against the concentration of CBP501 in the reaction. The quantity of phosphorylated substrate for each kinase reaction without CBP501 was nominated as 100%.

Example 4

Figure 2:
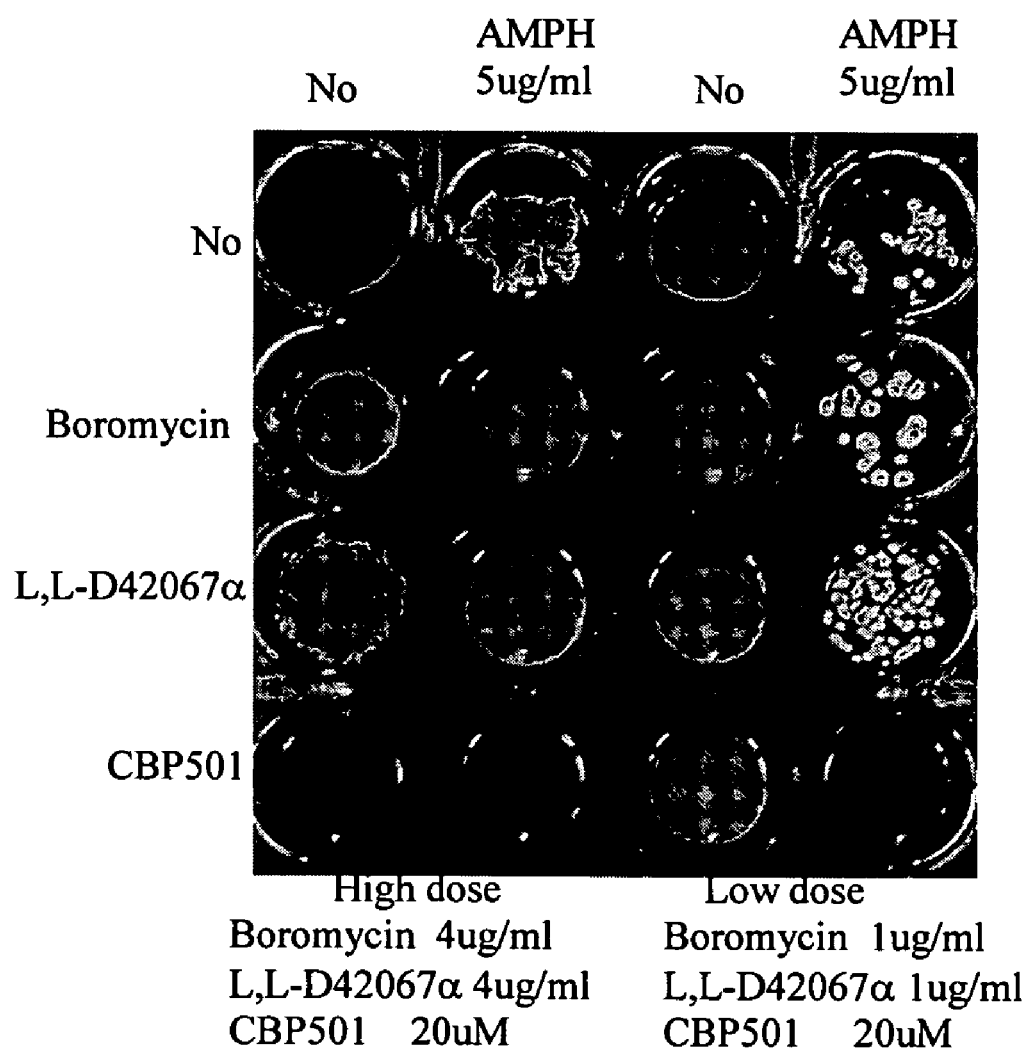
FIG. 2 shows anti-fungal activity of CBP501 with and without the anti-fungal agent amphotericin B.

This example shows the growth inhibition of yeast AH109 growth on YAPD plate by CBP501 (FIG. 2).

Logarithmically growing yeast AH109 in liquid medium (YAPD) was diluted to 1 to 10 with warm liquid YAPD medium with or without CBP501 and/or amphotericin B at the indicated doses. After 1 hr incubation at 30° whole solution was poured onto the YAPD agarose plate. The plate was then incubated 3 days and the samples were phtographed (FIG. 2).

Example 5

This example shows growth inhibition of *Candida albicans, Candida glabrata, Cryptococcus neoformans* and *Trichophyton mentagroohytes* by CBP501.

*Candida albicans* was obtained from ATCC (ATCC 10231) and cultured in fluid Sabouraud medium at 37 degree. The turbidity was measured one day after the innoculation and treatment with CBP501 at 0.03, 0.1, 0.3, 1, 3, 10, 30, 100 µg/ml. *Candida glabrata* was obtained from ATCC (ATCC 36583) and cultured in fluid Sabouraud medium at 28 degree. The turbidity was measured two days after the innoculation and treatment with CBP501 at 0.03, 0.1, 0.3, 1, 3, 10, 30, 100 µg/ml. *Cryptococcus neoformans* was obtained from ATCC (ATCC 24067) and cultured in fluid Sabouraud medium at 37 degree. The turbidity was measured two days after the innoculation and treatment with CBP501 at 0.03, 0.1, 0.3, 1, 3, 10, 30, 100 µg/ml. *Trichophyton mentagroohytes* was obtained from ATCC (ATCC 9533) and cultured in potato dextrose broth at 28 degree. The turbidity was measured three days after the innoculation and treatment with CBP501 at 0.03, 0.1, 0.3, 1, 3, 10, 30, 100 µg/ml. Minimal growth inhibitory concentrations were determined as the concentration of minimal CBP501 where the turbidity was not increased (Table 2).

TABLE 2

Anti-fungal activity of CBP501 against various fungi.

|  | MIC* of CBP501 |
|---|---|
| *Candida albicans* | 100 µg/ml |
| *Candida glabrata* | 30 µg/ml |
| *Cryptococcus neoformans* | 1 µg/ml |
| *Trichophyton mentagroohytes* | 100 µg/ml |

*MIC = minimul inhibitory concentration

What is claimed is:

1. A method of inhibiting or reducing fungal infection or fungal growth, comprising contacting the fungus or an object in contact with the fungus with an amount of a peptide or peptidomimetic comprising a sequence defined as:

(i) P6-P5-P4-P3-P2-P1; wherein
P1 is d- or l-Cha;
P2 is d- or l-Bpa, d- or l-Phe4NO2;
P3 is any amino acid;
P4 is d- or l-tryptophan;
P5 is any amino acid; and
P6 is d- or l-Bpa, d- or l-Phe4NO2;

(ii) or a prodrug thereof, sufficient to inhibit or reduce fungal infection or fungal growth.

2. The method of claim 1, wherein the peptide or peptidomimetic comprises (d-Bpa) (d-Ser)(d-Trp)(d-Ser)(d-Phe-2,3,4,5,6-F)(d-Cha), and has anti-fungal activity.

3. The method of claim 1, further comprising contacting with or exposing the fungus or object to a nucleic acid damaging agent or nucleic acid damaging treatment.

4. The method of claim 1, wherein the fungus or object is present in a subject.

5. The method of claim 1, wherein the fungus comprises a yeast, mold or slime.

6. The method of claim 5, wherein the yeast comprises *Candida* or *Saccharomyces*.

7. The method of claim 1, wherein the fungus or object is present in the environment, in a residential, commercial, industrial or community setting, or in an agricultural or horticultural setting.

8. A method of inhibiting or reducing contamination of an object or organism with a fungus comprising contacting the object or organism with an amount of a compound including a peptide or peptidomimetic comprising a sequence defined as:

(i) P6-P5-P4-P3-P2-P1;
wherein P1 is d- or l-Cha;
P2 is d- or l-(Phe-2,3,4,5,6-F), d- or l-Bpa, d- or l-Phe4NO2;
P3 is any amino acid;
P4 is d- or l-tryptophan;
P5 is any amino acid; and
P6 is d- or l-Bpa, d- or l-Phe4NO2;

(ii) or a prodrug thereof, sufficient to inhibit or reduce contamination of the object or organism.

9. The method of claim 8, further comprising contacting with or exposing the object or organism to a nucleic acid damaging agent or nucleic acid damaging treatment.

10. The method of claim 9, wherein the organism comprises a cell.

11. The method of claim 10, wherein the cell is a cultured cell.

12. The method of claim 9, wherein the organism is a human subject.

13. The method of claim 9, wherein the organism is a plant.

14. The method of claim 8, wherein the object is non-living.

15. The method of claim 8, wherein the object is an inorganic material or an organic material.

16. The method of claim 8, wherein the fungus comprises a yeast, mold or slime.

17. A method of treating fungal growth or fungal infection, comprising administering to a subject having or at risk of having fungal growth or fungal infection an amount of a compound comprising a sequence defined as:

(i) P6-P5-P4-P3-P2-P1;
wherein P1 is d- or l-Cha;
P2 is d- or l-(Phe-2,3,4,5,6-F), d- or l-Bpa, d- or l-Phe4NO2;
P3 is any amino acid;
P4 is d- or l-tryptophan;

P5 is any amino acid; and

P6 is d- or l-Bpa, d- or l-Phe4NO2;

(ii) or a prodrug thereof, effective to treat fungal growth or fungal infection.

18. The method of claim 17, wherein the peptide or peptidomimetic comprises (d-Bpa) (d-Ser)(d-Trp)(d-Ser)(d-Phe-2,3,4,5,6-F)(d-Cha), and has anti-fungal activity.

19. The method of claim 17, wherein the compound is administered locally, regionally or systemically.

20. The method of claim 17, wherein the compound is administered prior to, substantially contemporaneously with or following fungal contact, contamination, growth or infection.

21. The method of claim 17, wherein the compound is administered to skin, toe, nail, hair or a mucosal tissue.

22. The method of claim 17, wherein the fungal growth or fungal infection is present at least in part on the skin, toe, nail, hair or a mucosal tissue.

23. The method of claim 22, wherein the mucosal tissue is selected from the gastrointestinal tract, mouth, lungs, bronchial passages, nasal passages and sinuses, genitourinary tract, and vagina.

24. The method of claim 17, wherein the fungal growth or fungal infection comprises a yeast or mold.

25. The method of claim 17, wherein the fungal growth or fungal infection is selected from dermatophytes, *Coccidioides immitis, Histoplasma capsulatum, Candida albicans* and *Aspergillus fumigatus*.

26. The method of claim 17, wherein the fungal growth or fungal infection causes onychomycosis; Jock-itch or athlete's foot; paracoccidioidomycosis; blastomycosis; mucormycosis; cryptococcosis; coccidioidomycosis; histoplasmosis; candidiasis; or aspergillosis.

27. The method of claim 17, wherein the treatment results in improving the subject's condition.

28. The method of claim 27, wherein the improvement comprises reduced irritation, itching, inflammation, burning, hives, weeping, pruritus, excess discharge, discoloration, headache, or fatigue.

29. The method of claim 27, wherein the improvement comprises reduced susceptibility to or recurrence of fungal growth or fungal infection.

30. The method of claim 27, wherein the improvement comprises inhibiting a worsening or progression of the subject's condition.

31. The method of claim 27, further comprising administering a nucleic acid damaging agent, a nucleic acid damaging treatment, an anti-fungal agent, or an anti-fungal treatment to the subject.

32. The method of claim 31, wherein the agent or treatment comprises a drug.

33. The method of claim 32, wherein the drug comprises a chemotherapeutic drug.

34. The method of claim 32, wherein the drug has an anti-fungal activity or an anti-fungal function.

35. The method of claim 32, wherein the drug is a systemic drug or a topical drug.

36. The method of claim 32, wherein the drug is selected from a chemical class comprising: an allylamine, azole, polyene, pyrimidine, tetraene, thiocarbamate, sulfonamide, a glucan synthesis inhibitor and a benzoic acid compound.

37. The method of claim 32, wherein the drug is selected from amrolfine, butenafine, naftifine, terbinafine, ketoconazole, fluconazole, elubiol, econazole, econaxole, itraconazole, isoconazole, imidazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopirox olamine, haloprogin, undecylenate, silver sulfadiazine, undecylenic acid, undecylenic alkanolamide and Carbol-Fuchsin.

38. The method of claim 32, wherein the drug comprises 5-fluorouracil (5-FU), rebeccamycin, adriamycin (ADR), bleomycin (Bleo), pepleomycin, a cisplatin derivative, camptotecin (CPT), or a prodrug thereof.

39. A method of treating fungal growth, contamination or infection, comprising contacting a plant, plant part or seed having or at risk of having fungal growth, contamination or infection, with an amount of a sequence defined as:

(i) P6-P5-P4-P3-P2-P1;

wherein P1 is d- or l-Cha;

P2 is d- or l-(Phe-2,3,4,5,6-F), d- or l-Bpa, d- or l-Phe4NO2;

P3 is any amino acid;

P4 is d- or l-tryptophan;

P5 is any amino acid; and

P6 is d- or l-Bpa, d- or l-Phe4NO2;

(ii) or a prodrug thereof, effective to treat the fungal growth, contamination or infection.

40. The method of claim 39, wherein the peptide or peptidomimetic comprises (d-Bpa) (d-Ser)(d-Trp)(d-Ser)(d-Phe-2,3,4,5,6-F)(d-Cha), and has anti-fungal activity.

41. The method of claim 39, wherein the plant, plant part or seed is contacted with the sequence locally, regionally or systemically.

42. The method of claim 39, wherein the plant, plant part or seed is contacted with the sequence prior to, substantially contemporaneously with or following fungal growth, contamination or infection.

43. The method of claim 39, wherein the plant part comprises a leaf, stem, root, flower, seed, trunk or branch.

44. The method of claim 39, wherein the fungal growth, contamination or infection is present at least in part on the leaf, stem, root, flower, seed, trunk or branch.

45. The method of claim 39, wherein the fungal growth, contamination or infection is caused by a yeast, mold or slime.

46. The method of claim 39, wherein the fungal growth, contamination or infection is selected from black spot, *glomerella*, ripe spot, sooty blotch, *septoria* leaf spot, *cercospora* leaf spot, rust, downy mildew, brown rot, brown patch, a smut, verrucosisl, dead arm disease, *mycosphaerella* leaf spot, black spot (roses), flower blight, *septoria* leaf blight, early and late blight, leaf mould, anthracnose, ring spot, dollar spot, northern leaf blight, *alternaria* and leaspora spot.

47. The method of claim 39, wherein the treatment results in reducing, decreasing or inhibiting fungal growth, contamination, viability or infection.

48. The method of claim 39, wherein the treatment results in reduced susceptibility to or recurrence of fungal growth, contamination or infection.

49. The method of claim 39, wherein the treatment results in inhibiting a worsening or progression of the fungal growth, contamination or infection.

50. The method of claim 39, further comprising contacting the plant, plant part or seed with a nucleic acid damaging agent, a nucleic acid damaging treatment, an anti-fungal agent, or an anti-fungal treatment.

51. The method of claim 50, wherein the agent or treatment comprises a drug.

52. The method of claim 51, wherein the drug comprises a chemotherapeutic drug.

53. The method of claim 50, wherein agent or treatment has an anti-fungal activity or an anti-fungal function.

54. The method of claim 50, wherein agent or treatment is selected from, thiram, carboxin, mefenoxam, Dentachloronitrobenzene (PCNB), fludioxonil, thiabendazole, a copper-based fungicide, a sulfur compound, and a citrus oil.

55. The method of claim 51, wherein the drug comprises 5-fluorouracil (5-FU), rebeccamycin, adriamycin (ADR), bleomycin (Bleo), pepleomycin, a cisplatin derivative, camptotecin (CPT), or a prodrug thereof.

56. The method of claim 50, wherein the plant, plant part or seed is present in the environment, in an industrial setting, in a community setting, in a residential setting, in a commercial setting, or in an agricultural or horticultural setting.

57. The method of claim 1, wherein the peptide or peptidomimetic comprises a sequence set forth as (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg), and has anti-fungal activity.

58. The method of claim 8, wherein the peptide or peptidomimetic comprises a sequence set forth as (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg), and has anti-fungal activity.

59. The method of claim 17, wherein the peptide or peptidomimetic comprises a sequence set forth as (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg), and has anti-fungal activity.

60. The method of claim 39, wherein the peptide or peptidomimetic comprises a sequence set forth as (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg), and has anti-fungal activity.

61. The method of claim 50, wherein the agent or treatment comprises *Bacillus subtilis*.

* * * * *